US011377435B2

(12) United States Patent
Wang et al.

(10) Patent No.: US 11,377,435 B2
(45) Date of Patent: Jul. 5, 2022

(54) ENZYME-TRIGGERED CARBON MONOXIDE RELEASING MOLECULES

(71) Applicant: Georgia State University Research Foundation, Inc, Atlanta, GA (US)

(72) Inventors: Binghe Wang, Marietta, GA (US); Xingyue Ji, Suzhou (CN)

(73) Assignee: Georgia State University Research Foundation, Inc., Atlanta, GA (US)

( * ) Notice: Subject to any disclaimer, the term of this patent is extended or adjusted under 35 U.S.C. 154(b) by 5 days.

(21) Appl. No.: 16/712,639

(22) Filed: Dec. 12, 2019

(65) Prior Publication Data

US 2020/0115360 A1    Apr. 16, 2020

Related U.S. Application Data

(63) Continuation of application No. PCT/US2018/037123, filed on Jun. 12, 2018.

(60) Provisional application No. 62/518,467, filed on Jun. 12, 2017.

(51) Int. Cl.
*C07D 321/10*    (2006.01)
*C07D 265/30*    (2006.01)
*C07C 225/06*    (2006.01)
*A61P 9/00*    (2006.01)

(52) U.S. Cl.
CPC ............. *C07D 321/10* (2013.01); *A61P 9/00* (2018.01); *C07C 225/06* (2013.01); *C07D 265/30* (2013.01)

(58) Field of Classification Search
None
See application file for complete search history.

(56) References Cited

U.S. PATENT DOCUMENTS

| | | | |
|---|---|---|---|
| 6,242,644 | B1 | 6/2001 | Ackermann et al. |
| 10,300,069 | B2 | 5/2019 | Wang et al. |
| 10,751,344 | B2 | 8/2020 | Wang et al. |
| 2017/0128456 | A1 | 5/2017 | Wang et al. |

FOREIGN PATENT DOCUMENTS

| | | |
|---|---|---|
| WO | 2015191616 A1 | 12/2015 |
| WO | 2018093924 A1 | 5/2018 |

OTHER PUBLICATIONS

Grant & Hackh's Chemical Dictionary (5th Ed. 1987) at p. 148.*
Chemical Abstract Registry No. 79516-06-6, indexed in the Registry File on STN CAS Online Nov. 16, 1984.*
Motterlini et al., The therapeutic potential of carbon monoxide. Nature Reviews Drug Discovery, 2010, 9, 728-743.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Botov, et al. "Synthesis and Performance of Acyloxy-diene-Fe(CO)$_3$ Complexes with Variable Chain Lengths as Enzyme-Triggered Carbon Monoxide-Releasing Molecules." Organometallics. 2013;32:3587-3594.
Heinemann, et al. "Carbon monoxide-physiology, detection and controlled release." Chem Common. 2014;50:3644-3660.
Ji, et al. "Toward Carbon Monoxide Based Therapeutics: Critical Drug Delivery and Developability Issues." Journal of Pharmaceutical Sciences 105 (2016) 406-416.
Ji et al., "Click and Release: A Chemical Strategy toward Developing Gasotransmitter Prodrugs by Using an Intramolecular Diels-Alder Reaction", Angewandte Chemie International Edition, vol. 55, No. 51, Nov. 23, 2016, pp. 15846-15851.
Pan et al., "Organic CO Prodrugs: Structure-CO-Release Rate Relationship Studies", Chemistry—A European Journal, vol. 23, No. 41, May 25, 2017, pp. 9838-9845.
Peng, et al. "Visible-light activatable organic CO-releasing molecules (photoCORMs) that simultaneously generate fluorophores." Org Biomol Chem. 2013;11:6671-6674.
Romanski, et al. "Iron Dienylphosphate Tricarbonyl Complexes as Water-SolubleEnzyme-Triggered CO-Releasing Molecules (ET-CORMs)." Organometallics. 2012; 31:5800-5809.
Romanski, et al. "Acyloxvbutadiene tricarbonyl iron complexes as enzyme-triggered CO-releasing molecules (ET-CORMs): a structure-activity relationship study." Dalton Trans. 2012: 41:13862.
Schatzschneider. "Novel lead structures and activation mechanisms for CO-releasing molecules (CORM)." British Journal of Pharmacology. 2015; 172:1638-1650.
Stamellou, et al. "Different design of enzyme-triggered CO-releasing molecules (ET-CORMs) reveals quantitative differences in biological activities in terms of toxicity and inflammation." Redox Biology. 2014;2: 739-748.
Wang, et al. "3,6-substituted-1,2,4,5-tetrazines: tuning reaction rates for staged labeling applications." Org Biomol Chem. 2014;12:3950-3955.
Wang et al., "A Click-and-Release Approach to CO Prodrugs", Chemical Communications, vol. 50, No. 100, Oct. 31, 2014, pp. 15890-15893.
PCT/US2018/037123 , "International Search Report and Written Opinion", dated Aug. 27, 2018, 9 pages.

* cited by examiner

*Primary Examiner* — Po-Chih Chen
(74) *Attorney, Agent, or Firm* — Kilpatrick Townsend & Stockton LLP

(57) ABSTRACT

The present invention generally relates to carbon monoxide releasing compounds and compositions, and their use as carbon monoxide prodrugs. The compounds disclosed herein contain a cyclopentadienone moiety, a non-reactive dienophile, and an enzyme-cleavable tethering moiety connecting the cyclopentadienone moiety to the non-reactive dienophile. Cleavage of the enzyme-cleavable tethering moiety results in conversion of the non-reactive dienophile to a reactive dienophile.

12 Claims, 6 Drawing Sheets

COP-1

ENZYME-TRIGGERED CARBON MONOXIDE RELEASING MOLECULES

CROSS-REFERENCES TO RELATED APPLICATIONS

The present application is a continuation of International Pat Appl. No. PCT/US2018/037123, filed on Jun. 12, 2018, which claims priority to U.S. Provisional Pat. Appl. No. 62/518,467, filed on Jun. 12, 2017, which applications are incorporated herein by reference in their entirety.

STATEMENT AS TO RIGHTS TO INVENTIONS MADE UNDER FEDERALLY SPONSORED RESEARCH AND DEVELOPMENT

This invention was made with government support under Grant No. CA 180519 awarded by the National Institutes of Health. The government has certain rights in the invention.

BACKGROUND OF THE INVENTION

Carbon monoxide (CO) is well-known as a lethal, toxic gas. However, CO is also an important member of the gasotransmitter family of signaling molecules in mammalian systems whose importance is on par with that of NO and $H_2S$. NO was the first identified gaseous small molecule biological messenger in mammals. Nitroglycerin (glyceryl trinitrate) serves as an exogenous source of NO and is the most widely used drug for vasodilation and treatment of heart conditions.

CO also has beneficial therapeutic effects. The endogenous production of CO in a mammalian system occurs through the activity of heme oxygenases (HO-1 and HO-2). These enzymes regulate the catabolism of heme and play an important role in the modulation of a variety of responses, such as stress response and circadian rhythm. Studies have shown that CO has anti-inflammatory, anti-proliferative, and anti-apoptotic effects when the concentrations of CO in carrier gas (air) ranges from 10 to 250 ppm.

CO has been found to play a key beneficial role in various inflammatory and cardiovascular diseases. Among the various inflammatory related disorders, inflammatory bowel disease (IBD), psoriasis, mid-ear infection-induced inflammation, uveitis, and burn- and injury-related inflammation can be effectively treated by CO. For some of the inflammation related conditions, the detailed mechanism may not necessarily be entirely clear. For example, the pathogenesis of IBD is still unclear due to multiple factors involved in the inflammatory processes such as genetic mutations, bacterial infections, and physiological and immunological stress responses. Tumor necrosis factor alpha (TNF-α) plays a central role in the pathogenesis of IBD, as evidenced by the successful treatment of patients with anti-TNF-α antibodies in multiple clinical trials. The anti-inflammatory effects of CO have been reported using cell culture and animal models of sepsis. CO administration or HO-1 overexpression in RAW 264.7 cells inhibits TNF-α expression after treatment with lipopolysaccharide (LPS). In several inflammatory models, CO has been reported to inhibit Granulocyte-Macrophage Colony-Stimulating Factor (GM-CSF) expression, resulting in attenuation of inflammation. The effective and targeted treatments of IBD are largely limited due to significant systemic side effects. Until now, anti-inflammatory drugs and immunosuppressants are two options used in IBD treatment. There are some mitogen-activated protein kinase (MAPK) inhibitors being developed as treatment options. For other inflammation-related symptoms, the situation is similar. For example, psoriasis has limited effective treatment options, e.g., corticoid hormone and anti-TNFα.

Rheumatoid arthritis and osteoarthritis are two more examples of inflammatory disorders that can be treated with CO. Administration of CO from carbon monoxide releasing molecules (CORMs) in a model of collagen-induced arthritis suppressed the clinical and histopathological manifestations of the disease. The data is consistent with the reduction in the levels of inflammatory cytokines such as interleukins and TNF-α in joint tissue, and showed decreased cellular infiltration, joint inflammation and cartilage destruction.

Besides anti-inflammatory effects, evidence suggests that CO plays a beneficial role in treating cardiovascular disease. Pulmonary arterial hypertension (PAH), one type of pulmonary hypertension, is an incurable disease at this moment, and is described as high blood pressure in the arteries of the lungs. It is driven by an increased expansion of vascular smooth muscle in the pulmonary arterioles and leads to right heart hypertrophy and infarct. Breathing low concentrations of CO gas (e.g., 150 ppm) has been investigated as a treatment to improve pulmonary arterial hypertension and is currently in phase II clinical trials. Preliminary results have shown that after 16 weeks, the pulmonary vascular resistance has decreased 20% compared to the pre-therapy value. The mechanism of action of CO in the treatment of PAH has been reported as involving endothelial derived NO to induce apoptosis of the hyper-proliferative vascular smooth muscle cells.

A key issue in the use of CO as a therapeutic agent is the safe delivery of low doses to the desired site of action. A number of carbon monoxide releasing molecules (CORMs) have been investigated. Currently available CO delivery systems are metal-containing CORMs that can release CO, especially upon exposure to light and/or water. Manganese-based photo CORMs are representative of these molecules. However, for medicinal applications, especially for systemic administration, overcoming the toxicity of residual metal ions is a key issue.

Boric acid complexes have been investigated for non-photochemical approaches for the delivery of CO in vivo. In the case of CO delivery using UV irradiation, the rate of CO release is generally slow (half-life about 20-fold slower than that of metal-CORMs) and toxicity issues have limited the development of these compounds. Besides organometallic compounds, dialkylaldehydes, oxalates, boroncarboxylates and silacarboxylates are CORMs that are transition-metal free and can release CO under mild conditions. Boroncarboxylates are well known CO releasers and possess good water solubility. Disodium boranocarbonate, for example, has been used in animal models for disease treatment. Silacarboxylic acids ($R_3SiCOOH$) can deliver stoichiometric amounts of CO in the presence a nucleophile. However, toxicity issues and limited ability for chemical transformations make these molecules unsuitable candidates for therapeutic applications. Other organic molecules also release CO as a byproduct. However, these reactions are not easily controlled or necessitate the use of UV light to activate these molecules is a limitation in their application as medicinal agents.

Therefore, there is a need for molecules that can controllably release CO in vivo and in vitro with little or no toxicity and without the need for external stimuli. The present invention addresses this and other needs.

BRIEF SUMMARY OF THE INVENTION

In one aspect, the invention provides a compound comprising a cyclopentadienone moiety, a non-reactive dienophile, and an enzyme-cleavable tethering moiety connecting the cyclopentadienone moiety to the non-reactive dienophile. The cleavage of the enzyme-cleavable tethering moiety results in conversion of the non-reactive dienophile to a reactive dienophile.

In a related aspect, the invention provides a compound according to Formula I:

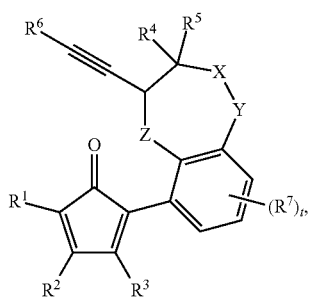
(I)

or a pharmaceutically acceptable salt thereof, wherein:

the moiety —X—Y— is selected from the group consisting of —C(O)—O— and —O—C(O)—;

Z is selected from the group consisting of —O— and —S—;

$R^1$ is selected from the group consisting of H, $C_{1-8}$ alkyl, $C_{3-8}$ cycloalkyl, $C_{6-10}$ aryl, and —C(O)$R^{1a}$;

$R^{1a}$ is selected from the group consisting of $C_{1-8}$ alkyl, $C_{3-8}$ cycloalkyl, $C_{6-10}$ aryl, 3- to 8-membered heterocyclyl, 5- to 12-membered heteroaryl, —N$R^{1b}R^{1c}$, —O$R^{1b}$, and a solubilizing moiety;

$R^{1b}$ and $R^{1c}$ are independently selected from H, $C_{1-8}$ alkyl, $C_{3-8}$ cycloalkyl, and a solubilizing moiety;

$R^2$ and $R^3$ are independently selected $C_{6-10}$ aryl, or $R^2$ and $R^3$ are optionally taken together to form a fused tricyclic moiety;

$R^4$, $R^5$, and $R^6$ are independently selected from the group consisting of H and $C_{1-6}$ alkyl;

$R^1$, $R^2$, $R^3$, $R^4$, $R^5$, and $R^6$ are optionally and independently substituted with one or more $R^7$;

each $R^7$ is independently selected from the group consisting of $C_{1-4}$ alkyl, halogen, —CN, —O$R^a$, —C(O)$R^b$, —C(O)O$R^a$, —OC(O)$R^b$, —N($R^a$)$_2$, —N$R^a$C(O)$R^b$, —C(O)N($R^a$)$_2$, —S(O)$R^b$, —S(O)$_2R^b$, —S(O)$_2$O$R^a$, —S(O)$_2$N($R^a$)$_2$, and —N$R^a$S(O)$_2R^b$;

each $R^a$ is independently selected from the group consisting of H and $C_{1-4}$ alkyl;

each $R^b$ is $C_{1-4}$ alkyl; and subscript t is 0, 1, 2, or 3.

In some embodiments, the invention provides a compound of Formula I, or a pharmaceutically acceptable salt thereof, wherein the moiety —X—Y— is —O—C(O)—. In some embodiments, $R^2$ and $R^3$ are taken together to form a fused tricyclic moiety.

In some embodiments, the compound of Formula I, or a pharmaceutically acceptable salt thereof, has a structure according to Formula Ia:

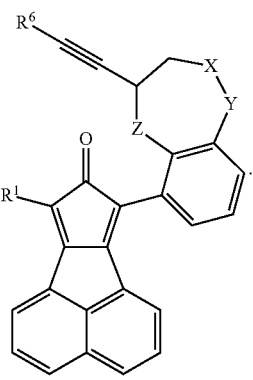
(Ia)

In some embodiments of the invention, the compound of Formula Ia, or a pharmaceutically acceptable salt thereof, has a structure according to Formula Ib:

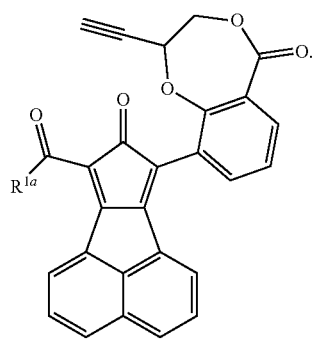
(Ib)

In some embodiments, the invention provides a compound of any one of the formulae described herein, or a pharmaceutically acceptable salt thereof, wherein:

$R^{1a}$ is selected from the group consisting of 3- to 8-membered heterocyclyl and —N$R^{1b}R^{1c}$;

$R^{1b}$ is selected from H and $C_{1-8}$ alkyl; and $R^{1c}$ is selected from H, $C_{1-8}$ alkyl, and a solubilizing moiety.

In some embodiments, the invention provides a compound of any one of the formulae described herein, or a pharmaceutically acceptable salt thereof, wherein the solubilizing moiety is selected from the group consisting of an moiety oligo(ethylene glycol), a poly(ethylene glycol) moiety, and a monosaccharide moiety.

In some embodiments, the invention provides a compound of Formula I, and pharmaceutically acceptable salts thereof, which is selected from the group consisting of:

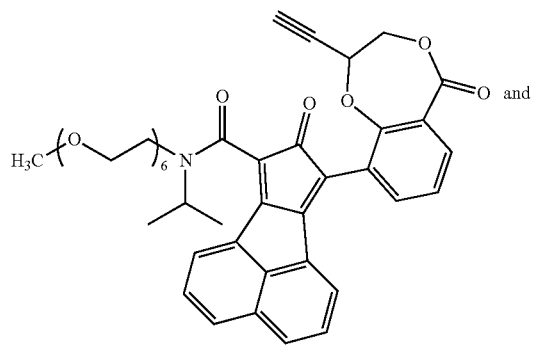
and

-continued

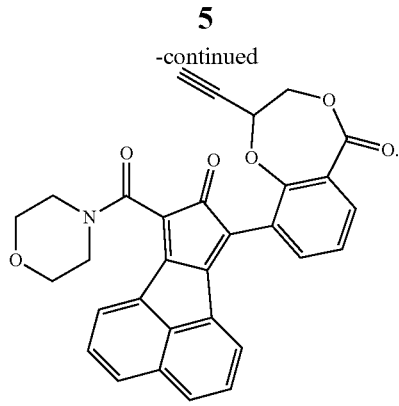

In another related aspect, the invention provides a pharmaceutical composition comprising a compound as described herein, or a pharmaceutically acceptable salt thereof, and a pharmaceutically acceptable excipient.

In another aspect, the invention provides a method for delivering carbon monoxide to a subject in need thereof. The method includes administering to the subject a compound or a pharmaceutical composition as described herein.

In another aspect, the invention provides a method for treating a disease or condition. The method includes administering to a subject in need thereof an effect amount of a compound or pharmaceutical composition as described herein. In some embodiments, the disease or condition is inflammation, cancer, organ transplantation, bacterial infection, or thrombosis.

DETAILED DESCRIPTION OF THE INVENTION

I. General

Figure 1:
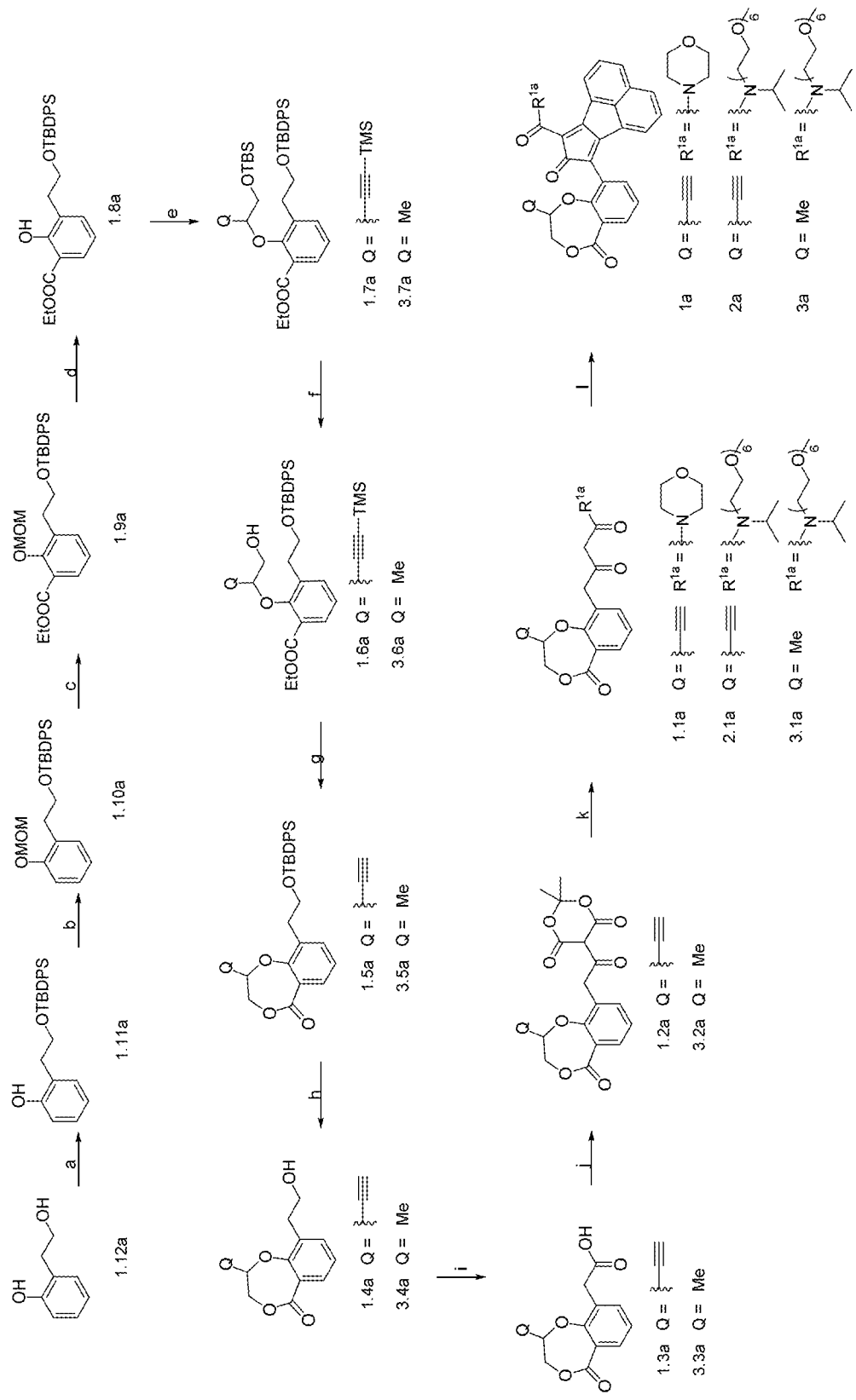
FIG. 1. Synthetic scheme for the preparation of exemplary compounds of the invention, 1a and 2a, and control compound 3a. Abbreviations and details for all synthetic steps are disclosed herein.

Described herein are enzyme-sensitive molecules that can controllably and selectively release CO in vivo and in vitro with little or no toxicity and without the need for external stimuli. Methods for treating diseases and conditions using the enzyme-sensitive carbon monoxide releasing compounds are also described.

II. Definitions

As used herein, the terms "compound" and "compound of the invention" are used interchangeably and refer to a molecule of the present invention comprising a cyclopentadienone moiety, a non-reactive dienophile or a reactive dienophile, and an enzyme-cleavable tethering moiety, which undergoes intramolecular cyclization to release carbon monoxide.

As used herein, the term "carbon monoxide" refers to :C≡O: and :C=O: as well as other forms of carbon monoxide formed under physiological conditions.

As used herein, the term "intramolecular cyclization" refers to the reaction between the cyclopentadienone moiety of a carbon monoxide releasing compound and the reactive dienophile of the same carbon monoxide releasing compound, leading to formation of a cyclic structure and concomitant release of carbon monoxide.

As used herein, the term "cycloaddition reaction" refers to a pericyclic chemical reaction, such as a Diels-Alder reaction, in which two or more unsaturated molecules or two unsaturated moieties within one molecule combine to form a cyclic adduct in which there is a net reduction of the bond multiplicity. The terms "Diels-Alder reaction" and "DAR" are used interchangeably and refer to a type of pericyclic chemical reaction, in which three pi-bonds are broken, and two sigma bonds and one new pi-bond are formed in a 6-membered ring.

As used herein, the term "cyclopentadienone moiety" refers to a moiety of a compound of the invention having the structure

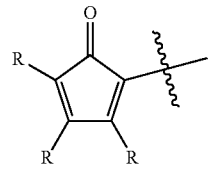

wherein R is H or another substituent as described herein. In some embodiments, R is $R^1$, $R^2$, and $R^3$ as defined below. The cyclopentadienone moiety of the carbon monoxide releasing compounds participates in a Diels-Alder reaction via cycloaddition with the reactive dienophile of the same compound under physiological conditions.

As used herein, the term "non-reactive dienophile" refers to a dienophile (e.g., alkene, alkyne) of a compound that is not capable of reacting with a cyclopentadienone moiety of the same compound under physiological conditions in the absence of a stimulus such as an enzyme.

As used herein, the term "reactive dienophile" refers to an alkene or alkyne moiety of a compound that is capable of participating in a Diels-Alder reaction via cycloaddition with a cyclopentadienone moiety of the same compound under physiological conditions. In general, a reactive dienophile is generated via scission of an enzyme-cleavable tethering moiety of the same compound, thereby converting a nonreactive dienophile to the reactive dienophile.

As used herein, the term "physiological conditions" refers to one or more of physiological temperature, pH, and tonicity. Body temperature is typically from about 33° C. to about 40° C., preferably from about 35° C. to about 38° C., such as about 37° C. Physiological pH is typically from about 6.8 to 8, preferably 6.8 to about 7.5, such as about 7.0. However, the pH may be lower or higher at specific sites and/or due to a particular disease state. For example, lower pH is often associated with diseased tissue such as tumor tissue.

As used herein, the term "enzyme" refers to a protein that catalyzes a chemical reaction. Enzymes can be endogenous or exogenous proteins. Enzymes include, but are not limited to, hydrolases, esterases, phosphatases, glycosidases, oxidases, reductases, lipases, transferases, polymerases and ligases. In some embodiments, the enzyme is a hydrolase. In some embodiments, the enzyme is an esterase. In some embodiments, the enzyme is a glycosidase. In some embodiments, the enzyme is a phosphatase. In some embodiments, the enzyme catalyzes an intramolecular cyclization reaction between the cyclopentadienone moiety and the dienophile of a compound by cleaving the enzyme-cleavable tethering moiety of the compound. The cleavage results in the conversion of the non-reactive dienophile to a reactive dienophile and concomitant release of carbon monoxide.

As used herein, the term "enzyme-cleavable tethering moiety" refers to functional group having a cleavable covalent bond (e.g., ester or amide). In some embodiments, the enzyme-cleavable tethering moiety has the general formulaic expression of "X—Y," wherein X and Y are defined as described herein. The enzyme-cleavable tethering moiety is susceptible to the scission of the bond between X and Y in the presence of a suitable enzyme described herein. Cleavage of the bond between X and Y converts the non-reactive dienophile to a reactive dienophile. As a non-limiting example, an esterase can cleave the bond between —C(O)— and —O— of a —C(O)—O— moiety.

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. Unless otherwise specified, "substituted alkyl" groups can be substituted with one or more groups selected from halo, hydroxy, amino, alkylamino, amido, acyl, nitro, cyano, and alkoxy.

As used herein, the term "alkoxy," by itself or as part of another substituent, refers to a group having the formula —OR, wherein R is alkyl as described above.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. Unless otherwise specified, "substituted cycloalkyl" groups can be substituted with one or more groups selected from halo, hydroxy, amino, alkylamino, amido, acyl, nitro, cyano, and alkoxy.

As used herein, the term "alkylene" refers to an alkyl group, as defined above, linking at least two other groups (i.e., a divalent alkyl radical). The two moieties linked to the alkylene group can be linked to the same carbon atom or different carbon atoms of the alkylene group.

As used herein, the terms "halo" and "halogen," by themselves or as part of another substituent, refer to a fluorine, chlorine, bromine, or iodine atom.

As used herein, the term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "aryl," by itself or as part of another substituent, refers to an aromatic ring system having any suitable number of carbon ring atoms and any suitable number of rings. Aryl groups can include any suitable number of carbon ring atoms, such as $C_6$, $C_7$, $C_8$, $C_9$, $C_{10}$, $C_{11}$, $C_{12}$, $C_{13}$, $C_{14}$, $C_{15}$ or $C_{16}$, as well as $C_{6-10}$, $C_{6-12}$, or $C_{6-14}$. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. Unless otherwise specified, "substituted aryl" groups can be substituted with one or more groups selected from halo, hydroxy, amino, alkylamino, amido, acyl, nitro, cyano, and alkoxy.

As used herein, the term "heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of heteroatoms can be included in the heteroaryl groups, such as 1, 2, 3, 4; or 5, or 1 to 2, 1 to 3, 1 to 4, 1 to 5, 2 to 3, 2 to 4, 2 to 5, 3 to 4, or 3 to 5. For example, heteroaryl groups can be $C_{5-8}$ heteroaryl, wherein 1 to 4 carbon ring atoms are replaced with heteroatoms; or $C_{5-8}$ heteroaryl, wherein 1 to 3 carbon ring atoms are replaced with heteroatoms; or $C_{5-6}$ heteroaryl, wherein 1 to 4 carbon ring atoms are replaced with heteroatoms; or $C_{5-6}$ heteroaryl, wherein 1 to 3 carbon ring atoms are replaced with heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. Unless otherwise specified, "substituted heteroaryl" groups can be substituted with one or more groups selected from halo, hydroxy, amino, alkylamino, amido, acyl, nitro, cyano, and alkoxy.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein, the term "heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of carbon ring atoms can be replaced with heteroatoms in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted. Unless otherwise specified, "substituted heterocyclyl" groups can be substituted with one or more groups selected from halo, hydroxy, amino, oxo, alkylamino, amido, acyl, nitro, cyano, and alkoxy.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "protecting group" (i.e., "PG") refers to a chemical moiety that renders a functional group (e.g., an amino group) unreactive, but is also removable so as to restore the amino group. Examples of protecting groups include, but are not limited to, ethers (e.g., methoxymethyl ether, p-methoxybenzyl ether, and the like); silyl ethers (e.g., trimethylsilyl ether, tert-butyldiphenylsilyl ether, and the like); benzyloxycarbonyl (Z or Cbz); 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Other protecting groups are known to those of skill in the art including, for example, those described by Green and Wuts (*Protective Groups in Organic Synthesis*, 4$^{th}$ Ed. 2007, Wiley-Interscience, New York).

As used herein, the term "carbonyl," by itself or as part of another substituent, refers to —C(O)—, i.e., a carbon atom double-bonded to oxygen and bound to two other groups in the moiety having the carbonyl.

As used herein, the term "amino" refers to a moiety —NR$_2$, wherein each R group is H or alkyl. An amino moiety can be ionized to form the corresponding ammonium cation. "Dialkylamino" refers to an amino moiety wherein each R group is alkyl.

As used herein, the term "sulfonyl" refers to a moiety —SO$_2$R, wherein the R group is alkyl, haloalkyl, or aryl. An amino moiety can be ionized to form the corresponding ammonium cation. "Alkylsulfonyl" refers to an amino moiety wherein the R group is alkyl.

As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)NR$_2$, wherein each R group is H or alkyl.

As used herein, the term "nitro" refers to the moiety —NO$_2$.

As used herein, the term "oxo" refers to an oxygen atom that is double-bonded to a compound (i.e., O═).

As used herein, the term "solubilizing moiety" refers to a moiety used to increase the solubility of a compounds of the invention in a solvent (e.g., water or an organic solvent). Examples of solubilizing moieties include, but are not limited to, sugars (monosaccharides, oligosaccharides, and polysaccharides); polyols (e.g., glycerol, propylene glycol, and the like), synthetic polymers (e.g., hydrophilic polymers such as oligo(ethylene glycol), poly(ethylene glycols) (PEGs), poly-trimethylene glycols, poly(N-isopropylacrylamides) (NIPAMs), polyvinylpyrrolidones, polyoxyethylene-polyoxypropylene block copolymers, and the like) and biopolymers (e.g., proteins, starch, cellulose, heparin, hyaluronic acid, and the like).

As used herein, the term "monosaccharide" refers to a sugar having a five-membered carbon backbone (i.e., a pentose) or a six-membered carbon backbone (i.e., a hexose). Examples of monosaccharides include, but are not limited to, glucose, ribose, fucose, xylose, arabinose, galactose, mannose, glucuronic acid, and iduronic acid. Monosaccharides also include pentoses and hexoses substituted with hydroxy groups, oxo groups, amino groups, acetylamino groups, and other functional groups.

As used herein, the term "oligosaccharide" refers to a compound containing at least two monosaccharides covalently linked together. Oligosaccharides include disaccharides, trisaccharides, tetrasaccharides, pentasaccharides, hexasaccharides, heptasaccharides, octasaccharides, and the like. Covalent linkages for linking sugars generally consist of glycosidic linkages (i.e., C—O—C bonds) formed from the hydroxyl groups of adjacent sugars. Linkages can occur between the 1-carbon (the anomeric carbon) and the 4-carbon of adjacent sugars (i.e., a 1-4 linkage), the 1-carbon and the 3-carbon of adjacent sugars (i.e., a 1-3 linkage), the 1-carbon and the 6-carbon of adjacent sugars (i.e., a 1-6 linkage), or the 1-carbon and the 2-carbon of adjacent sugars (i.e., a 1-2 linkage). Other linkages can be present in the oligosaccharide, depending on the particular sugar subunits present. Those of skill in the art will appreciate that a sugar can be linked within an oligosaccharide such that the glycosidic bond at the anomeric carbon is in the α- or β-configuration.

As used herein, the term "polysaccharide" generally refers to a compound containing 10 or more sugars linked together as described for oligosaccharides.

As used herein, the term "salt" refers to acid or base salts of the compounds of the invention. Illustrative examples of pharmaceutically acceptable salts include mineral acid salts (salts of hydrochloric acid, hydrobromic acid, phosphoric acid, and the like), organic acid salts (salts of acetic acid, propionic acid, glutamic acid, citric acid and the like) salts, and quaternary ammonium salts (salts of methyl iodide, ethyl iodide, and the like). It is understood that the pharmaceutically acceptable salts are non-toxic. Additional information on suitable pharmaceutically acceptable salts can be found in *Remington: The Science & Practice of Pharmacy*, 20th ed., Lippincott Williams & Wilkins, Philadelphia, Pa., 2000, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Compounds of the present invention include all tautomers and stereoisomers thereof, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Any compound or formula given herein, is intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$, respectively. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound when administered to a mammal, particularly a human. See, for example, Foster, "Deuterium Isotope Effects in Studies of Drug Metabolism," *Trends Pharmacol. Sci.* 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$, $^{3}H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

As used herein, the term "pharmaceutical composition" is intended to encompass a product comprising the specified ingredients in the specified amounts, as well as any product, which results, directly or indirectly, from combination of the specified ingredients in the specified amounts.

As used herein, the term "pharmaceutically acceptable excipient" refers to a substance that aids the administration of an active agent to a subject. By "pharmaceutically acceptable," it is meant that the excipient is compatible with the other ingredients of the formulation and is not deleterious to the recipient thereof. Pharmaceutical excipients useful in the present invention include, but are not limited to, binders, fillers, disintegrants, lubricants, glidants, coatings, sweeteners, flavors and colors.

As used herein, the terms "treat", "treating," and "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom. The treatment or amelioration of symptoms can be based on any objective or subjective parameter, including, e.g., the result of a physical examination.

As used herein, the terms "effective amount" and "therapeutically effective amount" refer to a dose of a compound, such as a carbon monoxide releasing compound, that brings about a result, e.g., a therapeutic effect, for which the compound was administered. When "effective amount" is used to describe an in vivo method, the desired result can refer to a therapeutic effect. When "effective amount" is used to describe an ex vivo method the desired results can refer to a detectable level of carbon monoxide. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); *Goodman & Gilman's The Pharmacological Basis of Therapeutics*, 11th Edition, 2006, Brunton, Ed., McGraw-Hill; and *Remington: The Science and Practice of Pharmacy*, 21st Edition, 2005, Hendrickson, Ed., Lippincott, Williams & Wilkins).

The terms "about" and "around," as used herein to modify a numerical value, indicate a close range surrounding that explicit value. If "X" were the value, "about X" or "around X" would indicate a value from 0.9X to 1.1X. "About X"

thus includes, for example, a value from 0.95X to 1.05X, or from 0.98X to 1.02X, or from 0.99X to 1.01X. Any reference to "about X" or "around X" specifically indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.07X, 1.08X, 1.09X, and 1.10X. Accordingly, "about X" and "around X" are intended to teach and provide written description support for a claim limitation of, e.g., "0.98X."

III. Carbon Monoxide Releasing Compounds

The carbon monoxide releasing compounds of the invention include a cyclopentadienone moiety, a non-reactive dienophile, and an enzyme-cleavable tethering moiety connecting the cyclopentadienone moiety to the non-reactive dienophile. Cleavage of the enzyme-cleavable tethering moiety results in conversion of the non-reactive dienophile to a reactive dienophile. Intramolecular cyclization via reaction of the reactive dienophile and the cyclopentadienone moiety leads to release of carbon monoxide from the cyclopentadienone moiety.

In certain embodiments, the invention provides a compound according to Formula I:

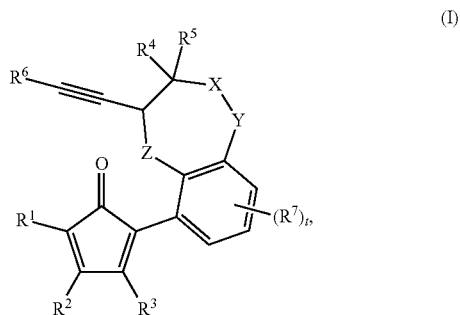

(I)

or a pharmaceutically acceptable salt thereof, wherein:
the moiety —X—Y— is selected from the group consisting of —C(O)—O— and —O—C(O)—;
Z is selected from the group consisting of —O— and —S—;
$R^1$ is selected from the group consisting of H, $C_{1-8}$ alkyl, $C_{3-8}$ cycloalkyl, $C_{6-10}$ aryl, and —C(O)$R^{1a}$;
$R^{1a}$ is selected from the group consisting of $C_{1-8}$ alkyl, $C_{3-8}$ cycloalkyl, $C_{6-10}$ aryl, 3- to 8-membered heterocyclyl, 5- to 12-membered heteroaryl, —NR$^{1b}$R$^{1c}$, —OR$^{1b}$, and a solubilizing moiety;
$R^{1b}$ and $R^{1c}$ are independently selected from H, $C_{1-8}$ alkyl, $C_{3-8}$ cycloalkyl, and a solubilizing moiety;
$R^2$ and $R^3$ are independently selected $C_{6-10}$ aryl, or $R^2$ and $R^3$ are optionally taken together to form a fused tricyclic moiety;
$R^4$, $R^5$, and $R^6$ are independently selected from the group consisting of H and $C_{1-8}$ alkyl;
$R^1$, $R^2$, $R^3$, $R^4$, $R^5$, and $R^6$ are optionally and independently substituted with one or more $R^7$;
each $R^7$ is independently selected from the group consisting of $C_{1-4}$ alkyl, halogen, —CN, —OR$^a$, —C(O)R$^b$, —C(O)OR$^a$, —OC(O)R$^b$, —N(R$^a$)$_2$, —NR$^a$C(O)R$^b$, —C(O)N(R$^a$)$_2$, —S(O)R$^b$, —S(O)$_2$R$^b$, —S(O)$_2$OR$^a$, —S(O)$_2$N(R$^a$)$_2$, and —NR$^a$S(O)$_2$R$^b$;
each $R^a$ is independently selected from the group consisting of H and $C_{1-4}$ alkyl;
each $R^b$ is $C_{1-4}$ alkyl; and
subscript t is 0, 1, 2, or 3.

$R^1$ in compounds of Formula I is generally selected from H, $C_{1-8}$ alkyl, $C_{3-8}$ cycloalkyl, $C_{6-10}$ aryl, and —C(O)$R^{1a}$. For example, $R^1$ can be H, methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, or branched octyl. In some embodiments, $R^1$ is selected from cyclopropyl, cyclobutyl, cyclopentyl, cyclohexyl, cycloheptyl, and cyclooctyl. In some embodiments, $R^1$ is selected from cyclobutyl, cyclopentyl, and cyclohexyl. In some embodiments, $R^1$ is selected from phenyl, naphthyl, and biphenyl. In some embodiments, $R^1$ is —C(O)$R^{1a}$.

$R^{1a}$ in compounds of Formula I is generally selected from $C_{1-8}$ alkyl, $C_{3-8}$ cycloalkyl, $C_{6-10}$ aryl, 3- to 8-membered heterocyclyl, 5- to 12-membered heteroaryl, —NR$^{1b}$R$^{1c}$, and a solubilizing moiety. For example, $R^{1a}$ can be methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, or branched octyl. In some embodiments, $R^{1a}$ is selected from cyclopropyl, cyclobutyl, cyclopentyl, cyclohexyl, cycloheptyl, and cyclooctyl. In some embodiments, $R^{1a}$ is selected from cyclobutyl, cyclopentyl, and cyclohexyl. In some embodiments, $R^{1a}$ is selected from piperazinyl, pyrrolidinyl, dioxanyl, morpholinyl, and tetrahydrofuranyl. In some embodiments, $R^{1a}$ is selected from pyrrolyl, pyridinyl, imidazolyl, pyrazolyl, triazolyl, pyrazinyl, triazinyl, indolyl, isoindolyl, and quinolinyl. In some embodiments, $R^{1a}$ is a solubilizing moiety. For example, $R^{1a}$ can be propylene glycol, an oligo(ethylene glycol), a poly(ethylene glycol), a poly(N-isopropylacrylamide), a polyvinylpyrrolidone, or a monosaccharide.

In some embodiments, $R^{1a}$ is NR$^{1b}$R$^{1c}$. Generally, $R^{1b}$ and $R^{1c}$ are independently selected from H, $C_{1-8}$ alkyl, $C_{3-8}$ cycloalkyl, and a solubilizing moiety. For example, $R^{1b}$ and $R^{1c}$ are independently selected from methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, and branched octyl. In some embodiments, $R^{1b}$ and $R^{1c}$ are independently selected from cyclopropyl, cyclobutyl, cyclopentyl, cyclohexyl, cycloheptyl, and cyclooctyl. In some embodiments, $R^{1b}$ and $R^{1c}$ are independently selected from cyclobutyl, cyclopentyl, and cyclohexyl. In some embodiments, $R^{1b}$ and $R^{1c}$ are independently selected from propylene glycol, an oligo(ethylene glycol), a poly(ethylene glycol), a poly(N-isopropylacrylamide), a polyvinylpyrrolidone, and a monosaccharide.

Generally, $R^2$ and $R^3$ in compounds of Formula I are independently-selected $C_{6-10}$ aryl groups, or $R^2$ and $R^3$ are optionally taken together to form a fused tricyclic moiety. For example, $R^2$ and/or $R^3$ can be selected from phenyl, naphthyl, and biphenyl. In some embodiments, $R^2$ and $R^3$ are taken together to form a fused tricyclic moiety.

Generally, $R^4$, $R^5$, and $R^6$ of Formula I are independently selected from the group consisting of H and $C_{1-8}$ alkyl. For example $R^4$, $R^5$, and $R^6$ can independently selected from H, methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, or branched octyl.

Each of the $R^1$, $R^2$, $R^3$, $R^4$, $R^5$, and $R^6$ substituents of Formula I are optionally and independently substituted with one or more $R^7$, wherein each $R^7$ is independently selected from the group consisting of $C_{1-4}$ alkyl, halogen, —CN, —OR$^a$, —C(O)R$^b$, —C(O)OR$^a$, —OC(O)R$^b$, —N(R$^a$)$_2$, NR$^a$C(O)R$^b$, —C(O)N(R$^a$)$_2$, —S(O)R$^b$, —S(O)$_2$R$^b$, —S(O)$_2$OR$^a$, —S(O)$_2$N(R$^a$)$_2$, and —NR'S(O)$_2$R$^b$. For example, each optional $R^7$ can independently be methyl, ethyl, n-propyl, isopropyl, n-butyl, sec-butyl, isobutyl, tert-butyl, fluorine atom, chlorine atom, bromine atom, or iodine atom.

Generally, each $R^a$ substituent is independently selected from the group consisting of H and $C_{1-4}$ alkyl. For example, each $R^a$ substituent can be H, methyl, ethyl, n-propyl, isopropyl, n-butyl, sec-butyl, isobutyl, or tert-butyl. Each $R^b$ substituent is an independently-selected $C_{1-4}$ alkyl group. For example, $R^b$ can be methyl, ethyl, n-propyl, isopropyl, n-butyl, sec-butyl, isobutyl, or tert-butyl.

In some embodiments, the invention provides compounds of Formula I, or pharmaceutically acceptable salts thereof, wherein the moiety —X—Y— is —O—C(O)— and $R^2$ and $R^3$ are taken together to form a fused tricyclic moiety.

In some embodiments, the invention provides compounds having a structure according to Formula Ia:

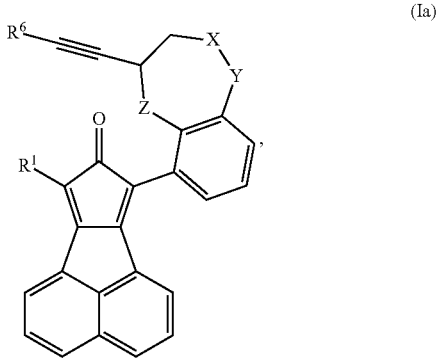

(Ia)

and pharmaceutically acceptable salts thereof.

In some embodiments, $R^1$ in compounds of Formula I and/or Formula Ia is selected from $C_{1-8}$ alkyl, $C_{3-8}$ cycloalkyl, $C_{6-10}$ aryl, and —C(O)$R^{1a}$. In some embodiments, $R^1$ is —C(O)$R^{1a}$. In some embodiments, $R^1$ in compounds of Formula I and/or Formula Ia is —C(O)$R^{1a}$ and $R^{1a}$ is selected from the group consisting of $C_{1-8}$ alkyl, $C_{3-8}$ cycloalkyl, $C_{6-10}$ aryl, 3- to 8-membered heterocyclyl, 5- to 12-membered heteroaryl, —NR$^{1b}$R$^{1c}$, and a solubilizing moiety. In some embodiments, $R^{1a}$ is selected from the group consisting of 3- to 8-membered heterocyclyl, 5- to 12-membered heteroaryl, and NR$^{1b}$R$^{1c}$.

In some embodiments, $R^6$ in compounds of Formula I and/or Formula Ia is H, methyl, ethyl, n-propyl, isopropyl, n-butyl, sec-butyl, isobutyl, tert-butyl, n-pentyl, branched pentyl, n-hexyl, or branched hexyl. In some embodiments, $R^6$ is H or methyl. In some embodiments, the moiety —X—Y— in compounds of Formula I and/or Formula Ia is —O—C(O)—.

In some embodiments, $R^1$ in compounds of Formula I and/or Formula Ia is —C(O)$R^{1a}$ and $R^{1a}$ is selected from the group consisting of pyridinyl, pyrimidinyl, piperidinyl, piperazinyl, and morpholino. In some embodiments, $R^6$ is selected from the group consisting of H and $C_{1-8}$ alkyl. In some such embodiments, the moiety —X—Y— is —O—C(O)—. In some such embodiments, Z is —O—.

In some embodiments, $R^1$ in compounds of Formula I and/or Formula Ia is —C(O)$R^{1a}$ and $R^{1a}$ NR$^{1b}$R$^{1c}$, wherein $R^{1b}$ and $R^{1c}$ are independently selected from $C_{1-8}$ alkyl and a solubilizing moiety. In some embodiments, $R^6$ is selected from the group consisting of H and $C_{1-8}$ alkyl. In some such embodiments, the moiety —X—Y— is —O—C(O)—. In some such embodiments, Z is —O—.

In some embodiments, $R^1$ in compounds of Formula I and/or Formula Ia is —C(O)$R^{1a}$ and $R^{1a}$ —NR$^{1b}$R$^{1c}$, $R^{1b}$ is selected from the group consisting of methyl, ethyl, n-propyl, and isopropyl, $R^{1c}$ is an oligo(ethylene glycol) or a poly(ethylene glycol). In some such embodiments, $R^6$ is selected from the group consisting of H and $C_{1-8}$ alkyl. In some such embodiments, the moiety —X—Y— is —O—C(O)—. In some such embodiments, Z is —O—.

In some embodiments, $R^1$ in compounds of Formula I and/or Formula Ia is —C(O)$R^{1a}$ and $R^{1a}$ is selected from the group consisting of 3- to 8-membered heterocyclyl and NR$^{1b}$R$^{1c}$. In some such embodiments, $R^6$ is selected from the group consisting of H, methyl, ethyl, n-propyl, isopropyl, n-butyl, sec-butyl, isobutyl, tert-butyl, n-pentyl, branched pentyl, n-hexyl, and branched hexyl. In some such embodiments, $R^6$ is selected from H and methyl. In some such embodiments, the moiety —X—Y— is —O—C(O)—. In some such embodiments, Z is —O—.

In some embodiments, $R^1$ in compounds of Formula I and/or Formula Ia is —C(O)$R^{1a}$, $R^{1a}$ is selected from the group consisting of pyridinyl, pyrimidinyl, piperidinyl, piperazinyl, and morpholino, $R^6$ is selected from the group consisting of H and $C_{1-8}$ alkyl, and the moiety —X—Y— is —O—C(O)—. In some such embodiments, Z is —O—.

In some embodiments, the compound, or pharmaceutically acceptable salt thereof, has a structure according to Formula Ib:

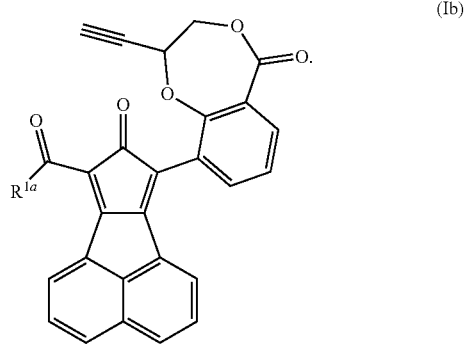

(Ib)

The $R^{1a}$ substituent of Formula I, Formula Ia and/or Formula Ib is generally selected from $C_{1-8}$ alkyl, $C_{3-8}$ cycloalkyl, $C_{6-10}$ aryl, 3- to 8-membered heterocyclyl, 5- to 12-membered heteroaryl, NR$^{1b}$R$^{1c}$, and a solubilizing moiety.

In some embodiments, $R^{1a}$ in compounds of Formula I, Formula Ia and/or Formula Ib are selected from $C_{3-8}$ cycloalkyl, $C_{6-10}$ aryl, 3- to 8-membered heterocyclyl, 5- to 12-membered heteroaryl, and NR$^{1b}$R$^{1c}$. In some embodiments, $R^{1a}$ is selected from 3- to 8-membered heterocyclyl, 5- to 12-membered heteroaryl, and NR$^{1b}$R$^{1c}$. In some embodiments, $R^{1a}$ is selected from 3- to 8-membered heterocyclyl and NR$^{1b}$R$^{1c}$.

In some embodiments, $R^{1a}$ is selected from cyclopropyl, cyclobutyl, cyclopentyl, cyclohexyl, cycloheptyl, and cyclooctyl. In some embodiments, $R^{1a}$ is selected from cyclobutyl, cyclopentyl, and cyclohexyl. In some embodiments, $R^{1a}$ is selected from piperazinyl, pyrrolidinyl, dioxanyl, morpholinyl, and tetrahydrofuranyl. In some embodiments, $R^{1a}$ is selected from pyrrolyl, pyridinyl, imidazolyl, pyrazolyl, triazolyl, pyrazinyl, triazinyl, indolyl, isoindolyl, and quinolinyl.

In some embodiments, $R^{1a}$ is $NR^{1b}R^{1c}$. Generally, $R^{1}b$ and $R^{1c}$ in compounds of Formula I, Formula Ia, and/or Formula Ib are independently selected from H, $C_{1-8}$ alkyl, $C_{3-8}$ cycloalkyl, and a solubilizing moiety. For example, $R^{1b}$ and $R^{1c}$ can be independently selected from methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, and branched octyl. In some embodiments, $R^{1b}$ and $R^{1c}$ are independently selected from cyclopropyl, cyclobutyl, cyclopentyl, cyclohexyl, cycloheptyl, and cyclooctyl. In some embodiments, $R^{1b}$ and $R^{1c}$ are independently selected from cyclobutyl, cyclopentyl, and cyclohexyl. In some embodiments, $R^{1b}$ and $R^{1c}$ are independently selected from propylene glycol, an oligo(ethylene glycol), a poly(ethylene glycol), a poly(N-isopropylacrylamide), a polyvinylpyrrolidone, and a monosaccharide.

In some embodiments, $R^{1b}$ in compounds of Formula I, Formula Ia, and/or Formula Ib is H or $C_{1-8}$ alkyl. For example, $R^{1b}$ can be H, methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, or branched octyl. In some embodiments, $R^{1c}$ of the $NR^{1b}R^{1c}$ moiety of Formula I, Formula Ia and/or Formula Ib is H, $C_{1-8}$ alkyl, or a solubilizing moiety. For example, $R^{1c}$ can be H, methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, or branched octyl. In some embodiments, $R^{1c}$ is propylene glycol, an oligo(ethylene glycol), a poly(ethylene glycol), a poly(N-isopropylacrylamide), a polyvinylpyrrolidone, or a monosaccharide. In some particular embodiments, $R^{1b}$ is methyl, ethyl, n-propyl, isopropyl, n-butyl, or sec-butyl, and $R^{1c}$ is a poly(ethylene glycol) or a poly(N-isopropylacrylamide). In some embodiments, $R^{1b}$ of $-NR^{1b}R^{1c}$ can be methyl, ethyl or isopropyl and $R^{1c}$ of $-NR^{1b}R^{1c}$ is selected from poly(ethylene glycol) (PEG) and poly(N-isopropylacrylamide) (NIPAM). In some particular embodiments, $R^{1b}$ of $-NR^{1b}R^{1c}$ can be isopropyl and $R^{1c}$ of $-NR^{1b}R^{1c}$ can be poly(ethylene glycol) (PEG) and poly(N-isopropylacrylamide) (NIPAM).

In some embodiments, the compound is selected from:

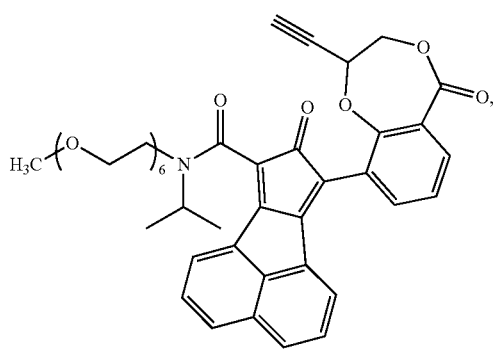

-continued

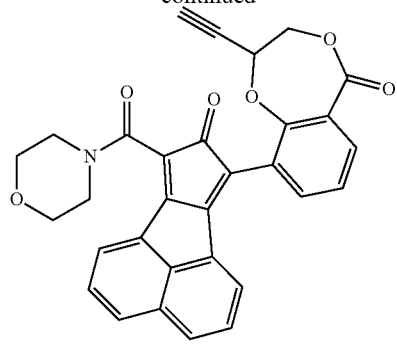

and pharmaceutically acceptable salts thereof.

IV. Synthesis of Carbon Monoxide Releasing Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). *Greene's protective groups in organic synthesis*. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$_{th}$ Edition, 2001), and Larock's Comprehensive Organic Transformations (VCH Publishers Inc., 1989).

Coupling agents are used when indicated for the following reactions. Suitable coupling agents (or activating agents) are known in the art and include for example, carbodiimides (e.g., N,N'-dicyclohexylcarbodiimide (DCC), N,N'-dicyclopentylcarbodiimide, N,N'-diisopropylcarbodiimide (DIC), 1-ethyl-3-(3-dimethylaminopropyl)carbodiimide (EDC), N-t-butyl-N-methylcarbodiimide (BMC), N-t-butyl-N-ethylcarbodiimide (BEC), 1,3-bis(2,2-dimethyl-1,3-dioxolan-4-ylmethyl)carbodiimide (BDDC), etc.), phosphonium salts (HOBt, PyBOP, HOAt, etc.), polymer-supported reagents (e.g., polymer-bound carbodiimide, polymer-bound TBTU, polymer-bound 2,4,6-trichloro-1,3,5-triazine, polymer-bound HOBt, polymer-bound HOSu, polymer-bound IIDQ, polymer-bound EEDQ, etc.), and the like (see, e.g., El-Faham, et al. *Chem. Rev.,* 2011, 111(11): 6557-6602; Han, et al. *Tetrahedron,* 2004, 60:2447-2467). Caboxylic acids where can also be converted to activated derivatives including, but not limited to, anhydrides (including symmetric, mixed, or cyclic anhydrides), activated esters (e.g., p-nitrophenyl esters, pentafluorophenyl esters, N-succinimidyl esters, and the like), acylazoles (e.g., acylimidazoles, prepared using carbonyl diimidazole, and the like), acyl azides, and acid halides (e.g., acid chlorides).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

Scheme 1

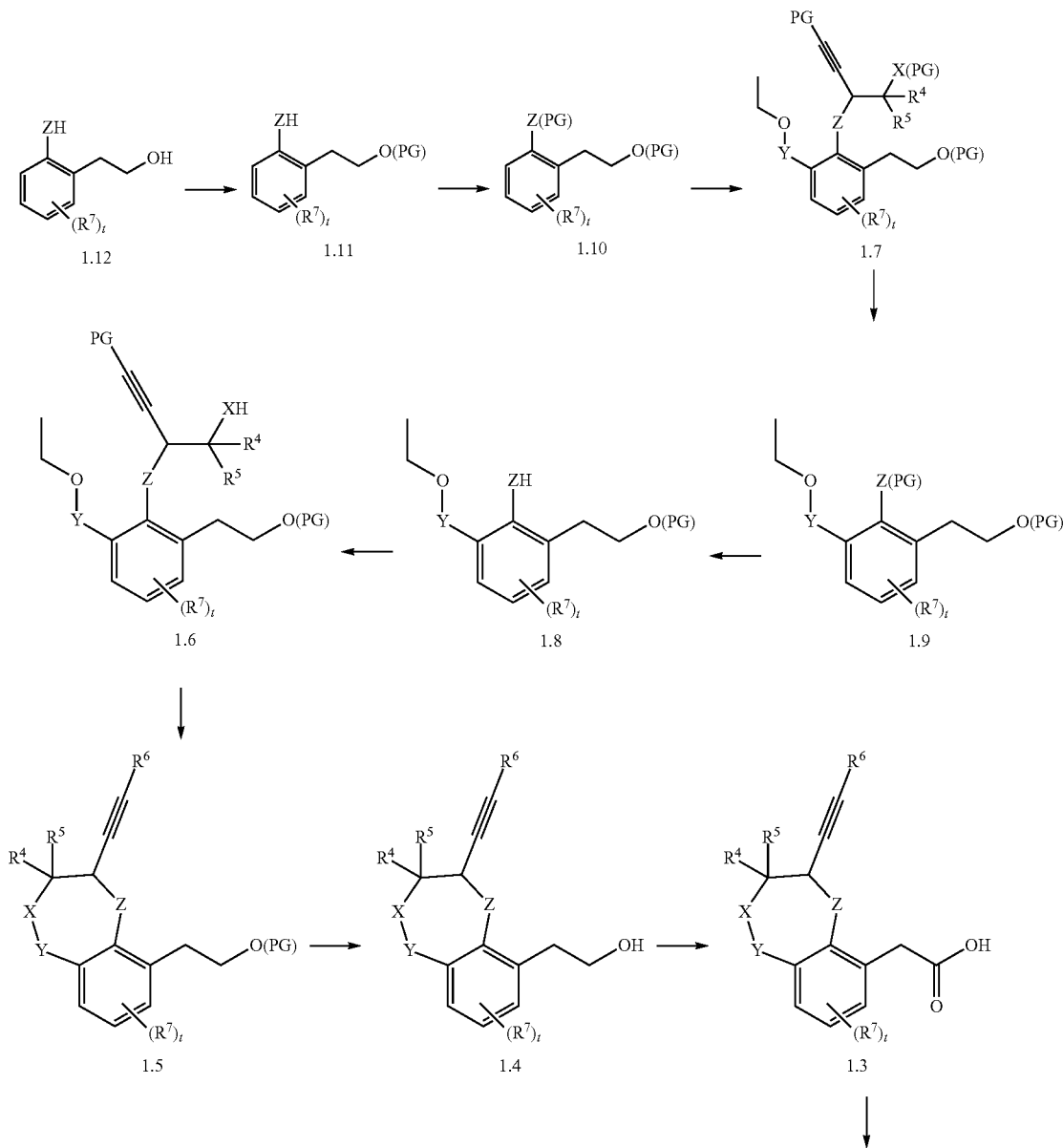

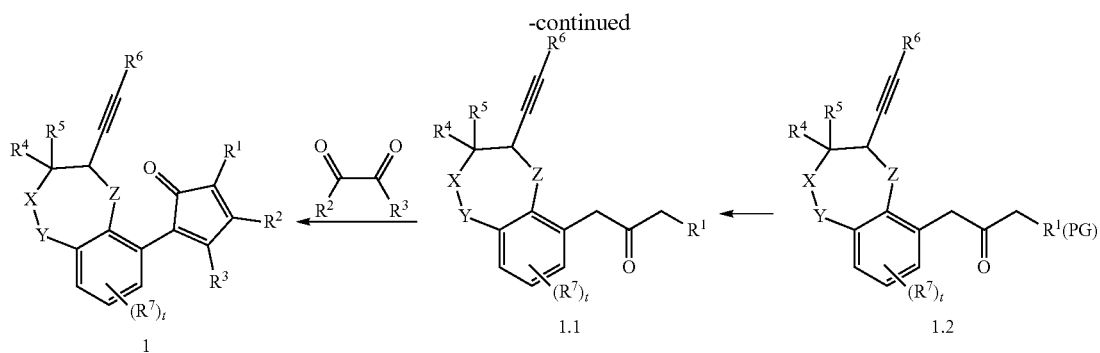

Scheme 1 above shows the general synthesis of the compounds of the invention (i.e., compounds of Formula I, Formula Ia and Formula Ib), wherein PG is an appropriate protecting group, and —X—Y—, Z, $R^1$, $R^2$, $R^3$, $R^4$, $R^5$, $R^6$, $R^7$ and t are as defined herein.

As depicted in Scheme 1, compounds may be prepared by contacting a suitably substituted 2-(2-hydroxyethyl)phenol or 2-(2-hydroxyethyl)thiophenol (1.12) with suitable protecting groups (PG), (e.g., a silyl either such as TBSO or an alkoxy ether) to form compounds of 1.11 and 1.10. Protected compound 1.10 can then undergo a nucleophilic substitution reaction using, for example, an organolithium reagent and a haloformate, to form compound 1.9. Selective deprotection of the Z(PG) moiety yields 1.8, which then undergoes a Mitsunobu reaction with a substituted alcohol to form compound 1.7. The selective deprotection of the —X(PG) moiety affords 1.6. After hydrolysis of the ester (—Y-OEt) of compound 1.6, subsequent lactonization can be carried out using a base (e.g., KOH), which is followed by the deprotection of the alkynyl moiety, affording compound 1.5. The hydroxyethyl substituent of 1.5 is deprotected to form compound 1.4, which is then oxidized using Jones' reagent to generate compound 1.3. Compound 1.3 can then be converted to compound 1.2 using a suitable coupling agent (e.g., EDC), which is then deprotected to form compound 1.1. Compound 1.1 is then condensed with a suitable 1,2-dione to afford compound 1.

V. Methods of Forming and Releasing Carbon Monoxide

In another aspect, the invention provides methods for forming and/or releasing carbon monoxide. The methods include contacting a carbon monoxide releasing compound as described herein with an enzyme; wherein the compound comprises a cyclopentadienone moiety, a non-reactive dienophile, and an enzyme-cleavable tethering moiety; and wherein the contacting is conducted under conditions sufficient to cleave the enzyme-cleavable tethering moiety and convert the non-reactive dienophile to a reactive dienophile. Cleavage of the tethering moiety provides for cyclization of the compound via reaction of the reactive dienophile with the cyclopentadienone moiety and concomitant release of carbon monoxide.

In some embodiments, the invention provides carbon monoxide releasing compounds which function by a mechanism shown in Scheme 2.

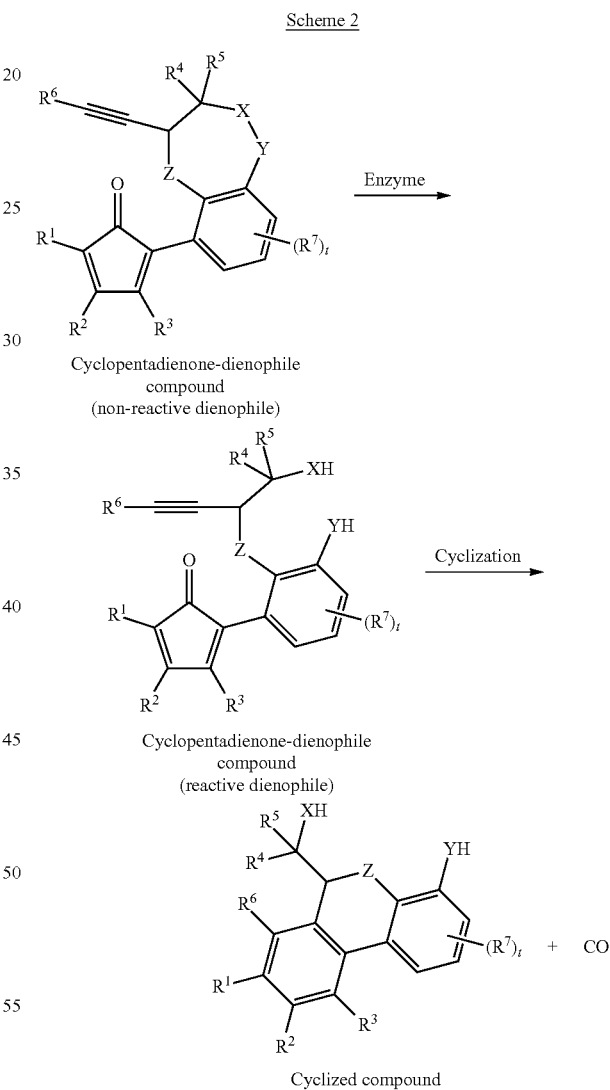

The methods of forming carbon monoxide generally include the formation of a reactive intermediate comprising a cyclopentadienone moiety, a reactive dienophile, and a cleaved tethering moiety. The reactive dienophile and the cyclopentadienone moiety of the same compound undergo intramolecular cyclization to form a cyclized compound upon the release of carbon monoxide.

In some embodiments, the enzyme is selected from a hydrolase, a phosphatase, an esterase, a glycosidase, an oxidase and a reductase. In some embodiments, the enzyme is an esterase. In general, the esterases in the methods of the invention catalyze the hydrolysis of ester bonds. Phosphatases catalyze the hydrolysis of phosphate bonds in the methods of the invention. Glycosidases catalyze the hydrolysis of glycosidic bonds in the methods of the invention. Proteases catalyze the hydrolysis of peptide bonds (i.e., amides) in the methods of the invention. In some embodiments, the hydrolysis promotes formation of a cyclized compound via intramolecular cycloaddition reaction of a reactive dienophile of a compound and a cyclopentadienone moiety of the same compound.

In certain embodiments, the invention provides a method of forming carbon monoxide wherein a compound of Formula I, Formula Ia, or Formula Ib is contacted with an enzyme so as to cleave the X—Y— moiety as described herein, thereby providing for cyclization of the alkyne with the cyclopentadienone to release carbon monoxide. The carbon monoxide can be formed and released in vitro, e.g., in a reaction mixture containing an enzyme and a compound as described herein. The carbon monoxide can also be formed and released in vivo, wherein a compound of the invention is cleaved by an endogenous enzyme in a subject following administration of the compound.

VI. Pharmaceutical Formulations

In a related aspect, the invention provides pharmaceutical compositions containing a compound (a compound of Formula I, Formula Ia and/or Formula Ib) of the invention and a pharmaceutically acceptable carrier or excipient, including but not limited to, purified water, buffer, or other pharmaceutically acceptable solvent. The carbon monoxide releasing compounds can also be formulated in a liposome or micelle. The amount of compound to be administered can be readily determined based on the amount of carbon monoxide to be generated.

The compounds can be administered orally, topically, parenterally, by inhalation or spray or rectally in dosage unit formulations. The term "administration by injection" includes intravenous, intramuscular, subcutaneous and parenteral injections, as well as use of infusion techniques. One or more compounds can be present in association with one or more non-toxic pharmaceutically acceptable carriers and if desired other active ingredients.

Parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes. The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride. More details on non-aqueous liquid formulations are disclosed below.

Solutions and dispersions of the carbon monoxide releasing compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Compositions intended for oral use can be prepared according to any suitable method known to the art for the manufacture of pharmaceutical compositions. Suitable oral dosage forms include tablets, capsules, solutions, suspensions, syrups, and lozenges. Such compositions can contain one or more agents selected from diluents, sweetening agents, flavoring agents, coloring agents and preserving agents in order to provide palatable preparations. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium carbonate, calcium sulfate, lactose, sucrose, mannitol, sorbitol, cellulose, microcrystalline cellulose, kaolin, sodium chloride, sodium phosphate, sodium carbonate, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrating and granulating agents are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross-linked polymers, such as cross-linked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Compositions for oral use can also be formulated as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the carbon monoxide releasing compounds in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents can be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the compounds in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example arachis oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Pharmaceutical compositions of the invention can also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol or sucrose. Such formulations can also contain a demulcent, a preservative and flavoring and coloring agents.

The compounds can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

VII. Methods of Treatment

The compounds (also referred to as carbon monoxide releasing compounds) and methods of the invention have applications in any therapeutic approach in which carbon monoxide requirements are addressed. The requirement may be due to deficiency of carbon monoxide in a subject. The compounds and methods can also be used to treat patients having normal levels of endogenous carbon monoxide but who would benefit from an increase in carbon monoxide. The invention therefore relates to methods for treating and preventing diseases that are mediated at least in part by endogenous carbon monoxide.

Accordingly, another aspect of the invention affords a method of providing carbon monoxide to a subject in need thereof. In certain embodiments, the method includes administering a compound of the invention, or a pharmaceutical composition containing a composition of the invention, to a subject under conditions sufficient to form carbon monoxide. In some embodiments, the method includes administering a compound according to Formula I to the subject. In some embodiments, the carbon monoxide releasing compounds are used for the treatment of a condition selected from a cardiovascular condition, an ophthalmic condition, a neurological condition, a urological condition, diabetes, inflammation, bacterial infection, hypertension, hypothermia, diabetes, asthma, gastric injury, irritable bowel syndrome, kidney dysfunction, sepsis, ischemia, respiratory distress syndrome, autoimmune disorders, thrombosis and cancer. The carbon monoxide releasing compounds can also be used for wound healing, organ preservation, and used to reduce rejection in organ transplantation (e.g., organ protection). In other embodiments, the compounds of the present invention can also be used to prevent, minimize, or reverse toxicity associated with the administration of various therapeutic agents, such as doxorubicin. As such, the compounds of the invention can be administered alone as a monotherapy or in combination with other active agents.

In some embodiments, the carbon monoxide releasing compounds are used for treatment of a cardiovascular condition. In some embodiments, the cardiovascular condition is selected from myocardial infarction, heart failure, heart attack, heart stroke, cardiomyopathy, myocardial fibrosis, pulmonary arterial hypertension (PAH), and angina pectoris.

In some embodiments, the carbon monoxide releasing compounds are used for treatment of cancers. In some embodiments, the cancer is selected from lung, breast, prostate, brain, bone, bladder, cervical, gastric, oral, ovarian, testicular, liver, rectal, retinal, urethral, uterine and vaginal cancer.

The cancer can be a carcinoma, a sarcoma, an adenocarcinoma, a lymphoma, a leukemia, and a solid and lymphoid cancer. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma, head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia, and multiple myeloma.

In some embodiments, the carbon monoxide releasing compounds are used for treatment of inflammatory disorders, including but not limited to, arthritis (i.e., rheumatoid arthritis and collagen-induced arthritis), inflammatory bowel disease (IBD), psoriasis, uveitis, mid-ear inflammation, and osteoarthritis. In some embodiments, the compounds are used for treatment of Alzheimer's disease. In some embodiments, the compounds are used for treatment of Parkinson's disease.

The specific dose level selected for any particular patient will depend upon a variety of factors, including the activity of the specific compound employed, the age, body weight, general health, sex, diet, time of administration, route of administration, and rate of excretion, drug combination and the severity of the condition undergoing therapy.

Carbon monoxide releasing compounds can be administered at any suitable dose in the methods of the invention. In general, a carbon monoxide releasing compound is administered at a dose ranging from about 0.1 milligrams to about 1000 milligrams per kilogram of a subject's body weight (i.e., about 0.1-1000 mg/kg). The dose of the carbon monoxide releasing compound can be, for example, about 0.1-1000 mg/kg, or about 1-500 mg/kg, or about 25-250 mg/kg, or about 50-100 mg/kg. The dose of the carbon monoxide releasing compound can be, for example, about 10-20 mg/kg, or 5-25 mg/kg, or 1-50 mg/kg, or 0.1-100 mg/kg. The dose of the compound can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg. The dose of the carbon monoxide releasing compound can be administered at a dose below about 1, below about 2, below about 3, below about 4, below about 5, below about 10, below about 15, below about 20, below about 25, below about 30, below about 35, below about 40, below about 45, below about 50, below about 55, below about 60, below about 65, below about 70, below about 75, below about 85, below about 90, below about 95, below about 100, below about 150, below about 200, below about 250, below about 300, below about 350, below about 400, below about 450, below about 500, below about 550, below about 600, below about 650, below about 700, below about 750, below about 800, below about 850, below about 900, below about 950, or below about 1000 mg/kg.

In some embodiments, the dose of the compound is sufficient to release carbon monoxide in an amount such that no more than about 20% of the hemoglobin in a blood sample obtained from the subject is present as carboxyhemoglobin (HbCO). In some embodiments, the dose of the compound is sufficient to release carbon monoxide in an amount such that no more than about 15% of the hemoglobin in a blood sample obtained from the subject is present as HbCO. In some embodiments, the dose of the compound is sufficient to release carbon monoxide in an amount such that the amount of HbCO in a blood sample taken from the subject ranges from about 5% to about 15% (e.g., from about 5-12%) based on the total amount of hemoglobin in the sample. Sampling and HbCO quantification can be conducted over periods of time ranging from minutes to hours, or longer, following compound administration, and HbCO concentrations can be determined using known quantitative methods and devices (as described, for example, in U.S. Pat. Nos. 6,397,093; 5,491,341; and 4,997,769). Dosage can be adjusted such that the peak HbCO concentration does not exceed a certain level (e.g., 15%).

The dosages can be varied depending upon the needs of the patient, the particular formulation being administered, and other factors. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to address the carbon monoxide requirement.

Administration of a compound of the present invention can be conducted for a period of time which will vary depending upon the nature of the particular carbon monoxide requirement, its severity and the overall condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a patient can be monitored for changes in his or her condition and for alleviation of the symptoms of the carbon monoxide requirement. The dosage of the carbon monoxide releasing compound can either be increased in the event the patient does not respond significantly to a particular dosage level, or the dose can be decreased if an alleviation of the symptoms of the carbon monoxide requirement is observed, or if the carbon monoxide requirement has been ablated, or if unacceptable side effects are seen with a particular dosage.

A therapeutically effective amount of carbon monoxide releasing compound can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 168, 192, 216, or 240 hours, or the equivalent amount of days. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be administered, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if the carbon monoxide requirement decreases, the dosage may be maintained or kept at lower than maximum amount. If the requirement increases, the first dosage regimen can be resumed until an improvement is seen, and the second dosing regimen can be implemented again. This cycle can be repeated multiple times as necessary.

One of skill in the art will appreciate that the administration of a carbon monoxide releasing compound of any of the disclosed embodiments can involve a carbon monoxide releasing compound comprising a cyclopentadienone moiety, a non-reactive dienophile, and an enzyme-cleavable tethering moiety and/or a carbon monoxide releasing compound comprising a cyclopentadienone moiety, a reactive dienophile, and a cleaved tethering moiety.

VIII. Examples

In general, all reagents and solvents used in the each step of the synthetic procedure of the carbon monoxide releasing compounds of the invention were of reagent grade. Column chromatography was carried out when necessary using flash silica gel (Sorbent 230-400 mesh) and P-2 Gel (Bio-Gel, particle size range 45-90 μm). Thin layer chromatography (TLC) analysis was conducted on silica gel plates (Sorbent Silica G UV254). Nuclear magnetic resonance (NMR) spectra were recorded at 400 MHz for $^1$H and 100 MHz for $^{13}$C on an Avance Bruker instrument. Chemical shifts (δ values) and coupling constants (J values) are given in ppm and hertz, respectively, using the respective solvent ($^1$H NMR, $^{13}$C NMR) as the internal reference.

Example 1

Synthesis of Compound 1.11a

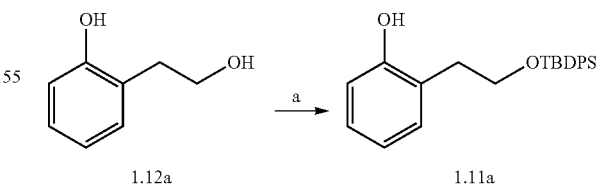

Compound 1.12a (2.0 g, 14.5 mmol) and imidazole (1.5 g, 21.7 mmol) were dissolved in anhydrous dimethylformamide (DMF) (10 mL) under $N_2$. Then, tert-butyldiphenylchlorosilane (TBDPSCl) (4.2 g, 15.2 mmol) was added dropwise at room temperature. The resulting mixture was stirred for another 1 h at room temperature. Then, the mixture was poured into water, and extracted with ethyl acetate (3×40 mL). The obtained organic layer was dried over anhydrous Na$_2$SO$_4$. After filtration and concentration, the residue was triturated with hexane, and the formed precipitate was filtered as the title compound 1.11a. Yield: 90%. $^1$H NMR (CDCl$_3$): δ 8.16 (s, 1H), 7.66 (d, J=6.8 Hz, 4H), 7.51-7.39 (m, 6H), 7.24 (t, J=7.2 Hz, 1H), 7.05 (d, J=7.6 Hz, 2H), 6.90 (t, J=7.2 Hz, 1H), 3.92 (t, J=5.2 Hz, 2H), 2.98 (t, J=5.2 Hz, 2H), 1.13 (s, 9H). $^{13}$C NMR (CDCl$_3$): δ 155.8, 135.6, 132.0, 130.9, 130.1, 128.4, 127.9, 126.9, 120.4, 117.1, 66.8, 35.1, 26.7, 18.9. HRMS (ESI) [M+Na]$^+$ calcd. for C$_{24}$H$_{28}$O$_2$SiNa 399.1756, found 399.1744.

Example 2

Synthesis of Compound 1.10a

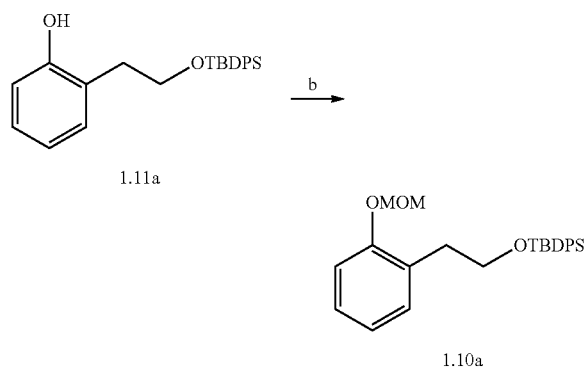

To a solution of compound 1.11a (1.5 g, 4 mmol) in dry DMF (25 mL) at 0° C. was added NaH (191 mg, 4.8 mmol) portion wise. Then the resulting mixture was stirred at 0° C. for another 0.5 h, followed by the dropwise addition of methoxymethyl chloride (MOMCl) (480 mg, 6 mmol). The resulting mixture was stirred for another 4 h at room temperature. The reaction mixture was poured into ice-water, and extracted with ethyl acetate (3×40 mL). The obtained organic layer was washed with brine, and dried over anhydrous Na$_2$SO$_4$. After filtration and concentration, the obtained residue was purified on a silica gel column to afford compound 1.10a as a colorless oil (yield: 90%). $^1$H NMR (CDCl$_3$): δ 7.76-7.61 (m, 4H), 7.54-7.37 (m, 6H), 7.28-7.20 (m, 2H), 7.17-7.06 (m, 1H), 6.99 (td, J=7.4, 1.1 Hz, 1H), 5.14 (s, 2H), 3.96 (t, J=7.2 Hz, 2H), 3.40 (s, 3H), 3.05 (t, J=7.2 Hz, 2H), 1.13 (s, 9H). $^{13}$C NMR (CDCl$_3$): δ 155.4, 135.6, 134.0, 131.4, 129.5, 127.6, 127.5, 121.4, 113.6, 94.1, 63.8, 55.9, 34.1, 26.8, 19.2. HRMS (ESI) [M+Na]$^+$ calcd. for C$_{26}$H$_{32}$O$_3$SiNa 443.2025, found 443.2018.

Example 3

Synthesis of Compound 1.9a

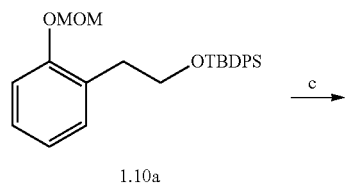

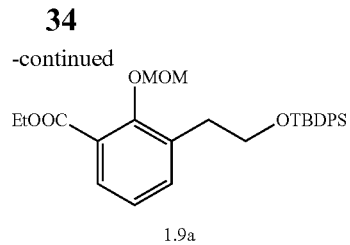

To a solution of compound 1.10a (1.0 g, 2.4 mmol) in anhydrous tetrahydrofuran (THF) (30 mL) at 0° C. was added tetramethylethylenediamine (TMEDA) (417 mg, 3.6 mmol), followed by the dropwise addition of n-butyllithium (n-BuLi) (1.8 mL, 3.6 mmol, 2M in hexane) under N$_2$. The resulting solution was stirred for another 1 h at room temperature. The obtained brownish solution was cooled to −78° C., followed by dropwise addition of ethyl chloroformate (520 mg, 4.8 mmol). A white precipitate was formed immediately. The resulting mixture was stirred with temperature slowly warming to room temperature (around 1 h). Then the reaction mixture was poured into saturated solution of NH$_4$Cl, and extracted with ethyl acetate (3×40 mL). The combined organic layer was dried over anhydrous Na$_2$SO$_4$. After filtration and concentration, the obtained residue was purified on a silica gel column to afford compound 1.9a as a colorless oil (yield: 78%). $^1$H NMR (CDCl$_3$): δ 7.74 (dd, J=7.6, 1.6 Hz, 1H), 7.64 (dd, J=8.0, 1.6 Hz, 4H), 7.49-7.33 (m, 7H), 7.10 (t, J=7.6 Hz, 1H), 5.03 (s, 2H), 4.40 (q, J=7.2 Hz, 2H), 3.95 (t, J=6.8 Hz, 2H), 3.54 (s, 3H), 3.06 (t, J=6.8 Hz, 2H), 1.43 (t, J=7.1 Hz, 3H), 1.07 (s, 9H). $^{13}$C NMR (CDCl$_3$): δ 166.4, 156.2, 135.6, 135.4, 133.9, 133.8, 129.7, 129.6, 127.6, 124.9, 123.6, 101.4, 63.8, 61.0, 57.4, 33.7, 26.9, 19.2, 14.3. HRMS (ESI) [M+Na]$^+$ calcd. for C$_{29}$H$_{36}$O$_5$SiNa 515.2238, found 515.2230.

Example 4

Synthesis of Compound 1.8a

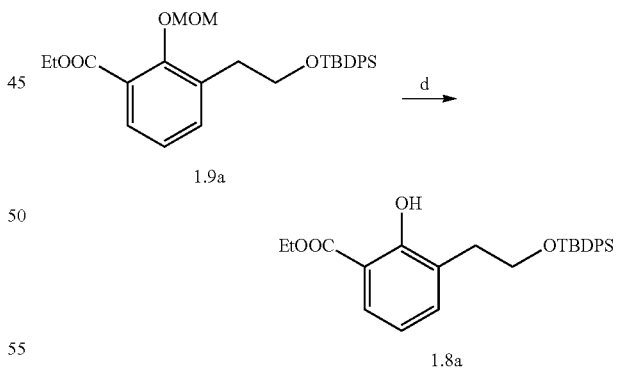

A solution of compound 1.9a (500 mg, 1.0 mmol) and CBr$_4$ (497 mg, 1.5 mmol) in isopropanol (20 mL) was heated under reflux for 3 h. Then the reaction mixture was dried, and purified on a silica gel column to afford compound 1.8a as a colorless oil (yield: 70%). $^1$H NMR (CDCl$_3$): δ 10.99 (s, 1H), 7.75 (dd, J=8.0, 1.7 Hz, 1H), 7.69-7.56 (m, 4H), 7.50-7.31 (m, 7H), 6.80 (t, J=7.7 Hz, 1H), 4.43 (q, J=7.1 Hz, 2H), 3.92 (t, J=6.7 Hz, 2H), 2.96 (t, J=6.7 Hz, 2H), 1.44 (t, J=7.1 Hz, 3H), 1.04 (s, 9H). $^{13}$C NMR (CDCl$_3$): δ 170.6, 160.1, 137.2, 135.6, 133.9, 129.5, 128.0, 127.6, 127.4, 118.3, 112.1, 62.9, 61.3, 33.3, 26.9, 19.2, 14.3. HRMS (ESI) [M+Na]$^+$ calcd. for C$_{27}$H$_{32}$O$_4$SiNa 471.1968, found 471.1984.

Example 5

Synthesis of Compounds 1.7a and 3.7a

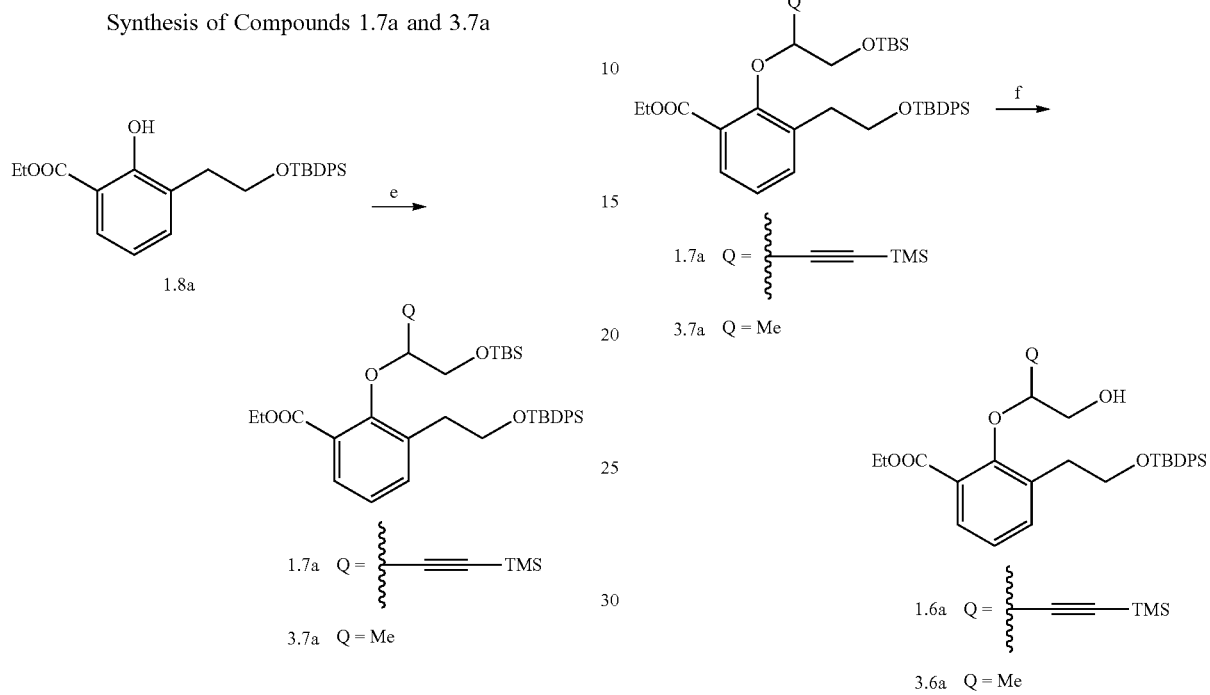

Example 6

Synthesis of Compounds 1.6a and 3.6a

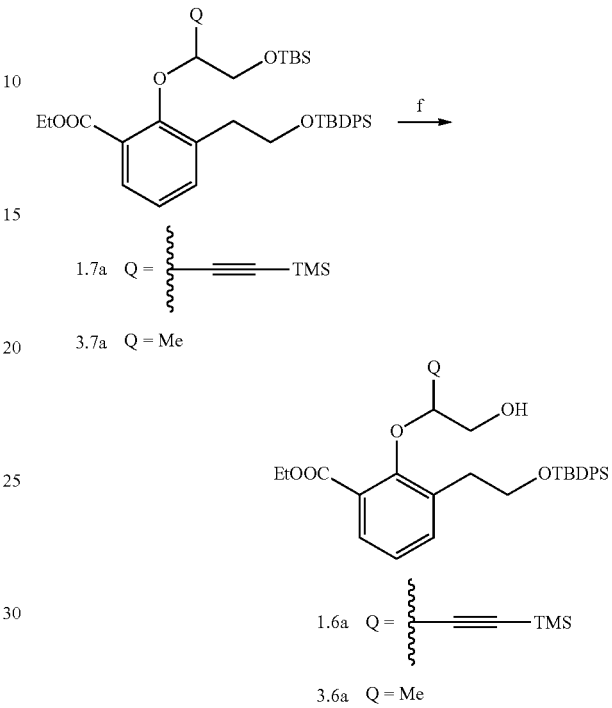

To a solution of compound 1.8a (1 equiv.), substituted alcohol (i.e., 1.7a. 1-((tert-butyldimethylsilyoxy)-4-(trimethylsilyl)but-3-yn-2-ol; 3.7a. 1-((tert-butyldimethylsilyl)oxy)propan-2-ol) (1.5 equiv.) and PPh$_3$ (1.5 equiv.) in dry THF under N$_2$ was added diisopropyl azodicarboxylate (DIAD) (1.5 equiv.) dropwise at 0° C. The resulting solution was stirred at room temperature overnight. The reaction mixture was poured into water, and extracted with ethyl acetate (3×40 mL). The combined organic layer was dried over anhydrous Na$_2$SO$_4$. After filtration and concentration, the residue was purified on a silica gel column to afford compound 1.7a or compound 3.7a as a pale-yellow oil.

Compound 1.7a (yield: 75%). $^1$H NMR (CDCl$_3$): δ 7.77 (dd, J=7.8, 1.8 Hz, 1H), 7.71-7.56 (m, 4H), 7.49-7.34 (m, 7H), 7.10 (t, J=7.6 Hz, 1H), 4.91 (t, J=5.6 Hz, 1H), 4.40 (q, J=7.2 Hz, 2H), 4.10-3.79 (m, 4H), 3.39 (dt, J=13.3, 6.5 Hz, 1H), 2.87 (dt, J=13.7, 6.9 Hz, 1H), 1.44 (t, J=7.2 Hz, 3H), 1.07 (s, 9H), 0.94 (s, 9H), 0.14 (s, 3H), 0.13 (s, 3H), 0.08 (s, 9H). $^{13}$C NMR (CDCl$_3$): δ 166.6, 155.2, 135.7, 135.6, 135.2, 135.1, 133.9, 133.8, 129.9, 129.5, 127.7, 127.6, 125.4, 123.6, 101.8, 93.2, 75.0, 65.7, 63.9, 60.9, 33.7, 26.9, 25.9, 19.2, 18.4, 14.3, −0.4, −5.2, −5.2. HRMS (ESI) [M+H]$^+$ calcd. for C$_{40}$H$_{58}$O$_5$Si$_3$Na 725.3490, found 725.3500.

Compound 3.7a (yield: 76%). $^1$H NMR (CDCl$_3$): δ 7.65-7.61 (m, 5H), 7.48-7.32 (m, 8H), 7.02 (t, J=7.6 Hz, 1H), 4.38 (q, J=6.8 Hz, 2H), 4.16-4.03 (m, 1H), 3.91-3.72 (m, 3H), 3.59 (dd, J=10.2, 5.9 Hz, 1H), 3.08-2.95 (m, 2H), 1.41 (t, J=7.1 Hz, 3H), 1.23 (d, J=6.2 Hz, 3H), 1.05 (s, 9H), 0.86 (s, 9H), 0.02 (s, 6H). $^{13}$C NMR (CDCl$_3$): δ 167.2, 155.7, 135.6, 134.8, 134.1, 133.9, 129.5, 127.6, 125.0, 122.6, 81.0, 66.1, 63.8, 60.9, 33.4, 26.8, 25.8, 21.6, 19.2, 18.2, 16.9, 14.3, −5.4. HRMS (ESI) [M+H]$^+$ calcd. for C$_{36}$H$_{52}$O$_5$Si$_2$Na 643.3251, found 643.3243.

To a solution of compound 1.7a or compound 3.7a (6 mmol) in THF (30 mL) was added 10% HCl (5 mL), and the resulting solution was stirred for 3 h at room temperature. The reaction mixture was extracted with ethyl acetate. The combine organic layer was washed with NaHCO$_3$ solution and brine successively, and was dried over anhydrous Na$_2$SO$_4$. After filtration and concentration, the residue was purified on a silica gel column to afford compound 1.6a or compound 3.6a as a colorless oil.

Compound 1.6a (Yield: 82%). $^1$H NMR (CDCl$_3$): δ 7.79 (dd, J=7.8, 1.8 Hz, 1H), 7.65 (dd, J=7.9, 1.5 Hz, 2H), 7.60 (dd, J=8.0, 1.5 Hz, 2H), 7.49-7.33 (m, 7H), 7.12 (t, J=7.7 Hz, 1H), 4.86 (dd, J=6.3, 3.9 Hz, 1H), 4.42-4.35 (m, 2H), 3.99-3.81 (m, 4H), 3.48-3.36 (m, 2H), 2.89-2.82 (m, 1H), 1.41 (t, J=7.1 Hz, 3H), 1.05 (s, 9H), 0.08 (s, 9H). $^{13}$C NMR (CDCl$_3$): δ 166.5, 155.6, 135.6, 135.5, 135.1, 133.7, 133.7, 129.9, 129.6, 129.6, 127.7, 127.6, 124.8, 123.9, 100.2, 94.4, 75.6, 65.6, 63.9, 61.3, 34.2, 26.8, 19.2, 14.3, −0.5. HRMS (ESI) [M+H]$^+$ calcd. for C$_{34}$H$_{44}$O$_5$Si$_2$Na 611.2625, found 611.2635.

Compound 3.6a (Yield: 84%). $^1$H NMR (CDCl$_3$): δ 7.71 (d, J=7.8 Hz, 1H), 7.65-7.60 (m, 4H), 7.50-7.32 (m, 7H), 7.08 (t, J=7.6 Hz, 1H), 4.48-4.34 (m, 2H), 4.25-4.09 (m, 1H), 3.95-3.86 (m, 2H), 3.74 (d, J=11.8 Hz, 1H), 3.60 (dd, J=11.9, 5.6 Hz, 1H), 3.09-2.89 (m, 2H), 1.41 (t, J=7.0 Hz, 3H), 1.17 (d, J=6.3 Hz, 3H), 1.05 (s, 9H). $^{13}$C NMR (CDCl$_3$): δ 167.0, 155.8, 135.6, 135.3, 134.2, 133.7, 133.6, 129.7, 129.6, 127.7, 127.6, 125.0, 123.2, 81.5, 65.9, 63.7, 61.4, 33.5, 26.8, 19.2, 16.0, 14.2. HRMS (ESI) [M+H]$^+$ calcd. for C$_{30}$H$_{38}$O$_5$SiNa 529.2386, found 529.2360.

Example 7

Synthesis of Compounds 1.5a and 3.5a

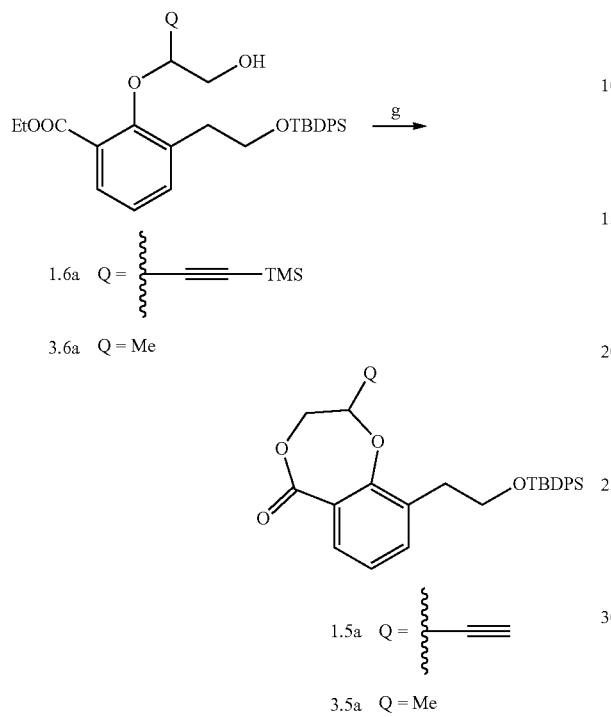

A solution of compound 1.6a or compound 3.6a (1 equiv.) and KOH (2 equiv.) in methanol and water was stirred at room temperature for 4 h at room temperature. The reaction mixture was poured into ice/water, and was acidified with 10% HCl to adjust the pH value to around 2. Then the mixture was extracted with ethyl acetate (3×40 mL). The combined organic layer was washed with $NaHCO_3$ solution and brine successively, and was dried over anhydrous $Na_2SO_4$. After filtration and concentration, the residue was dissolved in $Ac_2O$, and was heated under reflux for 1 h. Then reaction mixture was dried, and the residue was purified on a silica gel column to afford compound 1.5a or compound 3.5a as colorless oil.

Compound 1.5a (Yield: 70%). $^1$H NMR ($CDCl_3$): δ 7.65-7.62 (m, 3H), 7.56-7.53 (m, 3H), 7.47-7.29 (m, 6H), 7.20 (t, J=7.6 Hz, 1H), 5.22 (ddd, J=10.0, 4.4, 2.0 Hz, 1H), 4.35 (dd, J=13.6, 4.4 Hz, 1H), 4.23 (dd, J=13.6, 10.0 Hz, 1H), 3.98-3.92 (m, 1H), 3.88-3.82 (m, 1H), 3.32 (dt, J=12.5, 6.0 Hz, 1H), 2.88 (dt, J=13.8, 7.1 Hz, 1H), 2.50 (d, J=2.0 Hz, 1H), 1.05 (s, 9H). $^{13}$C NMR ($CDCl_3$): δ 169.2, 149.8, 136.9, 135.6, 135.5, 133.8, 133.6, 133.5, 129.9, 129.6, 127.7, 124.8, 124.5, 70.3, 66.8, 63.7, 33.4, 26.9, 19.2. HRMS (ESI) [M+H]$^+$ calcd. for $C_{29}H_{30}O_4SiNa$ 493.1811, found 493.1829.

Compound 3.5a (Yield: 74%). $^1$H NMR ($CDCl_3$): δ 7.67 (d, J=7.6 Hz, 1H), 7.59 (d, J=7.3 Hz, 2H), 7.56 (d, J=7.3 Hz, 2H), 7.48-7.31 (m, 7H), 7.11 (t, J=7.6 Hz, 1H), 4.50 (br, 1H), 4.21 (d, J=13.4 Hz, 1H), 4.04 (dd, J=13.4, 5.5 Hz, 1H), 3.87 (q, J=6.0 Hz, 2H), 3.03-2.98 (m, 1H), 2.91-2.86 (m, 1H), 1.32 (d, J=6.4 Hz, 3H), 1.04 (s, 9H). $^{13}$C NMR ($CDCl_3$): δ 169.9, 151.9, 136.5, 135.5, 133.7, 133.6, 131.9, 130.6, 129.6, 127.6, 123.3, 122.7, 99.9, 68.7, 63.6, 33.5, 26.8, 19.2, 17.7. HRMS (ESI) [M+H]$^+$ calcd. for $C_{28}H_{32}O_4SiNa$ 483.1968, found 483.1965.

Example 8

Synthesis of Compounds 1.4a and 3.4a

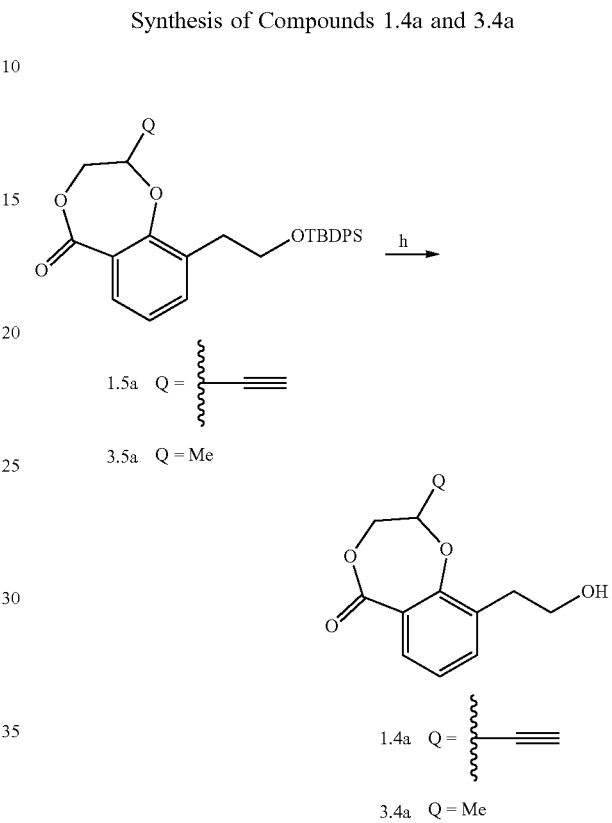

To a solution of compound 1.5a or compound 3.5a (1 equiv.) in THF was added a solution of tetra-n-butylammonium fluoride (TBAF) (1.5 equiv.) in THF, and the resulting solution was stirred for 2-3 h. The reaction mixture was poured into ice/water, and extracted with ethyl acetate (3×40 mL). The combined organic layer was dried over anhydrous $Na_2SO_4$. After filtration and concentration, the residue was purified on a silica gel column to afford compound 1.4a or compound 3.4a as colorless oil.

Compound 1.4a (Yield: 90%). $^1$H NMR ($CDCl_3$): δ 7.56 (d, J=7.7 Hz, 1H), 7.50 (d, J=7.5 Hz, 1H), 7.19 (t, J=7.6 Hz, 1H), 5.39-5.22 (m, 1H), 4.38 (dd, J=13.6, 4.3 Hz, 1H), 4.24 (dd, J=13.4, 10.3 Hz, 1H), 3.89-3.74 (m, 2H), 3.29-3.23 (m, 1H), 2.85-2.79 (m, 1H), 2.66 (s, 1H), 2.23 (br, 1H). $^{13}$C NMR ($CDCl_3$): δ 169.2, 149.8, 136.2, 133.3, 129.9, 125.2, 124.6, 77.3, 70.5, 66.8, 62.6, 33.2. HRMS (ESI) [M+H]$^+$ calcd. for $C_{13}H_{12}O_4Na$ 255.0633, found 255.0632.

Compound 3.4a (Yield: 85%). $^1$H NMR ($CDCl_3$): δ 7.62 (d, J=7.6 Hz, 1H), 7.46 (d, J=7.6 Hz, 1H), 7.13 (t, J=7.6 Hz, 1H), 4.71-4.67 (m, 1H), 4.31 (dd, J=13.5, 2.8 Hz, 1H), 4.14 (dd, J=13.5, 5.8 Hz, 1H), 3.82 (t, J=6.5 Hz, 2H), 3.00 (dt, J=13.3, 6.6 Hz, 1H), 2.86 (dt, J=13.4, 6.5 Hz, 1H), 1.43 (d, J=6.5 Hz, 3H). $^{13}$C NMR ($CDCl_3$): δ 169.9, 151.8, 135.9, 131.9, 130.6, 123.8, 123.2, 68.7, 62.6, 33.5, 17.7. HRMS (ESI) [M+H]$^+$ calcd. for $C_{12}H_{14}O_4Na$ 245.0790, found 245.0794.

Example 9

Synthesis of Compounds 1.3a and 3.3a

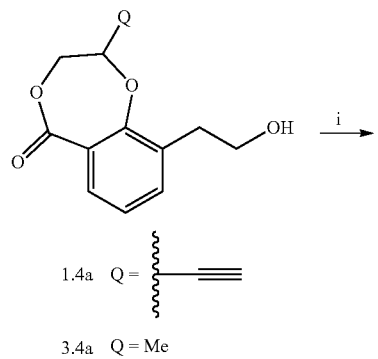

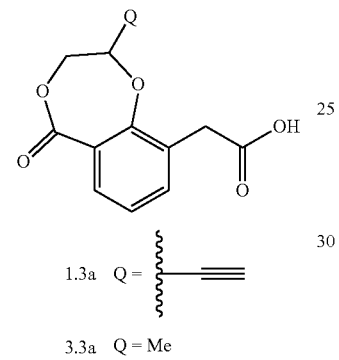

To a solution of compound 1.4a or compound 3.4a (1 equiv.) in acetone was added Jones' reagent (prepared from 250 mg $CrO_3$, 0.25 mL $H_2SO_4$, and 0.75 mL $H_2O$) until the reaction mixture gave a reddish solution at 0° C. Then reaction mixture was stirred for another 3 h at room temperature. The reaction mixture was then poured into icy water, and extracted with ethyl acetate (3×40 mL). The combined organic layer was dried over anhydrous $Na_2SO_4$. After filtration and concentration, the residue was purified on a silica gel column to compound 1.3a or compound 3.3a as white solid.

Compound 1.3a (Yield: 65%). $^1$H NMR ($CD_3OD$): δ 7.65 (dd, J=7.6, 1.6 Hz, 1H), 7.61 (dd, J=7.6, 1.6 Hz, 1H), 7.29 (t, J=7.6 Hz, 1H), 5.41 (ddd, J=9.0, 4.2, 2.2 Hz, 1H), 4.52 (dd, J=13.7, 4.2 Hz, 1H), 4.31 (dd, J=13.7, 9.0 Hz, 1H), 4.01 (d, J=16.8 Hz, 1H), 3.70 (d, J=16.8 Hz, 1H), 3.23 (d, J=2.2 Hz, 1H). $^{13}$C NMR ($CD_3OD$): δ 173.5, 169.7, 150.2, 136.4, 130.2, 129.4, 124.6, 124.4, 77.8, 77.1, 70.8, 66.9, 34.8. HRMS (ESI) [M−H]$^-$ calcd. for $C_{13}H_9O_5$ 245.0450, found 245.0444.

Compound 3.3a (Yield: 68%). $^1$H NMR ($CDCl_3$): δ 7.76 (d, J=7.8 Hz, 1H), 7.46 (d, J=7.4 Hz, 1H), 7.15 (t, J=7.6 Hz, 1H), 4.78-4.65 (m, 1H), 4.35 (d, J=13.6 Hz, 1H), 4.21 (dd, J=13.6, 5.4 Hz, 1H), 3.77 (d, J=16.4 Hz, 1H), 3.66 (d, J=16.4 Hz, 1H), 1.44 (d, J=6.8 Hz, 3H). $^{13}$C NMR ($CDCl_3$): δ 177.0, 169.4, 152.3, 136.2, 132.3, 126.7, 123.3, 121.9, 77.8, 68.8, 35.8, 17.7. HRMS (ESI) [M−H]$^-$ calcd. for $C_{12}H_{11}O_5$ 235.0606, found 235.0617.

Example 10

Synthesis of Compounds 1.2a and 3.2a

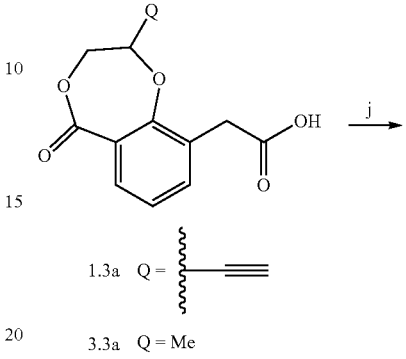

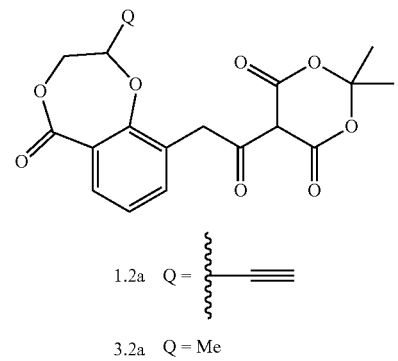

To a solution of compound 1.3a or compound 3.3a (1 equiv.), 2,2-dimethyl-1,3-dioxane-4,6-dione (1.4 equiv.), and 4-dimethylaminopyridine (DMAP) (1.4 equiv.) in DCM was added 1-ethyl-3-(3-dimethylaminopropyl)carbodiimide (EDC) (1.4 equiv.) portion wise at 0° C. The resulting mixture was stirred overnight at room temperature. Then the reaction mixture was diluted with DCM (30 mL), and washed with HCl 5% solution and brine successively. The obtained organic layer was dried over anhydrous $Na_2SO_4$. After filtration and concentration, the residue was purified on a silica gel column to afford compound 1.2a or compound 3.2a as yellow solid.

Compound 1.2a (Yield: 75%). $^1$H NMR ($CDCl_3$) δ 15.46 (s, 1H), 7.73 (dd, J=7.7, 1.7 Hz, 1H), 7.52 (dd, J=7.6, 1.6 Hz, 1H), 7.28 (t, J=7.6 Hz, 1H), 5.33-5.30 (m, 1H), 4.88 (d, J=17.5 Hz, 1H), 4.46-4.42 (m, 2H), 4.33 (dd, J=13.7, 9.7 Hz, 1H), 2.67 (d, J=2.2 Hz, 1H), 1.80 (s, 3H), 1.78 (s, 3H). $^{13}$C NMR ($CD_3OD$): δ 171.6, 170.2, 150.6, 136.7, 129.4, 124.4, 124.1, 101.9, 77.7, 77.4, 70.8, 67.3, 60.2, 25.0, 19.5, 13.1. HRMS (ESI) [M−H]$^-$ calcd. for $C_{19}H_{15}O_8$ 371.0767, found 371.0760.

Compound 3.2a (Yield: 73%). $^1$H NMR ($CD_3OD$): δ 7.54 (d, J=7.6 Hz, 1H), 7.38 (br, 1H), 7.11 (t, J=7.2 Hz, 1H), 4.63 (br, 1H), 4.39-4.31 (m, 2H), 4.16-4.05 (m, 2H), 1.64 (s, 6H), 1.35 (d, J=6.0 Hz, 3H). $^{13}$C NMR ($CD_3OD$): δ 195.7, 171.6, 171.1, 166.8, 152.5, 136.2, 131.3, 130.8, 129.6, 123.0, 102.2, 101.7, 89.3, 77.6, 68.9, 60.1, 42.5, 24.9, 19.5, 16.7, 13.1. HRMS (ESI) [M−H]$^-$ calcd. for $C_{18}H_{17}O_8$ 361.0923, found 361.0915.

Example 11

Synthesis of Compounds 1.1a, 2.1a and 3.1a

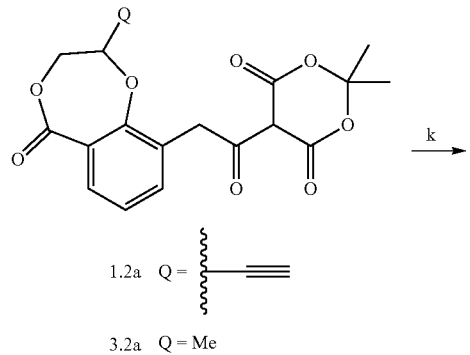

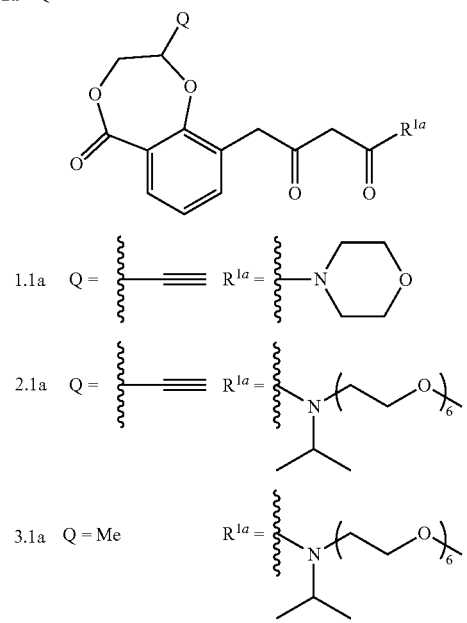

A solution of compound 1.2a or compound 3.2a (1 equiv.), amine (i.e., 1.1a. morpholine; 2.1a and 3.1a. N-isopropyl-2,5,8,11,14,17-hexaoxanonadecan-19-amine) (2 equiv.), and trimethylsilyl chloride (TMSCl) (3 equiv.) in toluene was heated under reflux for 2 h, then the reaction mixture was diluted with ethyl acetate (30 mL), and washed with NaHCO$_3$ solution and brine successively. The obtained organic layer was dried over anhydrous Na$_2$SO$_4$. After filtration and concentration, the residue was purified on a silica gel column to afford compound 1.1a, compound 2.1a or compound 3.1a as yellowish oil.

Compound 1.1a (Yield: 75%). $^1$H NMR (CDCl$_3$): δ 7.69 (d, J=7.7 Hz, 1H), 7.53 (d, J=7.5 Hz, 1H), 7.39-7.08 (m, 1H), 5.37-5.17 (m, 1H), 4.44 (dd, J=13.6, 4.1 Hz, 1H), 4.35-4.18 (m, 2H), 3.85 (d, J=17.1 Hz, 1H), 3.68-3.61 (m, 8H), 3.45-3.30 (m, 2H), 2.72 (s, 1H). $^{13}$C NMR (CDCl$_3$): δ 200.9, 168.5, 164.9, 149.9, 136.9, 131.3, 128.3, 125.4, 124.4, 78.1, 70.7, 66.7, 66.6, 48.4, 46.8, 44.3, 42.2. HRMS (ESI) [M+H]$^+$ calcd. for C$_{19}$H$_{19}$NO$_6$Na 380.1110, found 380.1110.

Compound 2.1a (Yield: 70%). $^1$H NMR (CD$_3$OD): δ 7.66 (t, J=8.1 Hz, 1H), 7.56 (t, J=6.7 Hz, 1H), 7.31 (t, J=7.6 Hz, 1H), 5.42-5.39 (m, 1H), 4.70-4.40 (m, 2H), 4.41-4.19 (m, 2H), 4.05-3.71 (m, 3H), 3.70-3.56 (m, 19H), 3.51-3.39 (m, 2H), 3.36 (s, 3H), 3.33 (br, 3H), 1.25-1.18 (m, 6H). $^{13}$C NMR (CD$_3$OD): δ 202.6, 201.7, 169.5, 169.5, 168.9, 167.7, 150.2, 136.8, 136.7, 130.6, 130.5, 129.0, 128.8, 124.8, 124.7, 124.4, 124.3, 78.4, 78.2, 77.3, 77.2, 71.6, 70.4, 70.2, 70.1, 70.0, 69.9, 68.4, 66.9, 57.71, 49.7, 49.1, 48.3, 44.2, 43.8, 43.6, 40.4, 20.0, 19.9, 19.1, 19.0. HRMS (ESI) [M+H]$^+$ calcd. for C$_{31}$H$_{45}$NO$_{11}$Na 630.2890, found 630.2878.

Compound 3.1a (Yield: 74%). $^1$H NMR (CDCl$_3$): δ 7.79-7.55 (m, 1H), 7.45 (d, J=7.4 Hz, 1H), 7.15-7.10 (m, 1H), 4.63-4.55 (m, 1H), 4.33 (dd, J=13.6, 5.2 Hz, 1H), 4.16 (dd, J=13.6, 5.2 Hz, 1H), 4.0-3.81 (m, 2H), 3.71-3.45 (m, 26H), 3.45-3.14 (m, 5H), 1.40 (d, J=6.5 Hz, 3H), 1.16 (d, J=5.7 Hz, 6H). $^{13}$C NMR (CDCl$_3$): δ 202.4, 201.8, 171.9, 169.5, 169.4, 167.4, 166.3, 152.3, 152.2, 136.6, 136.5, 131.9, 131.8, 127.7, 127.4, 123.6, 123.5, 122.5, 122.4, 77.8, 77.7, 71.9, 70.8, 70.7, 70.6, 70.5, 70.4, 68.8, 68.7, 68.6, 59.02 49.4, 48.9, 48.6, 46.4, 44.8, 44.7, 43.7, 40.7, 21.2, 20.4, 17.7. HRMS (ESI) [M+H]$^+$ calcd. for C$_{30}$H$_{47}$NO$_{11}$Na 620.3047, found 620.3043.

Example 12

Synthesis of Compounds 1a, 2a, and 3a

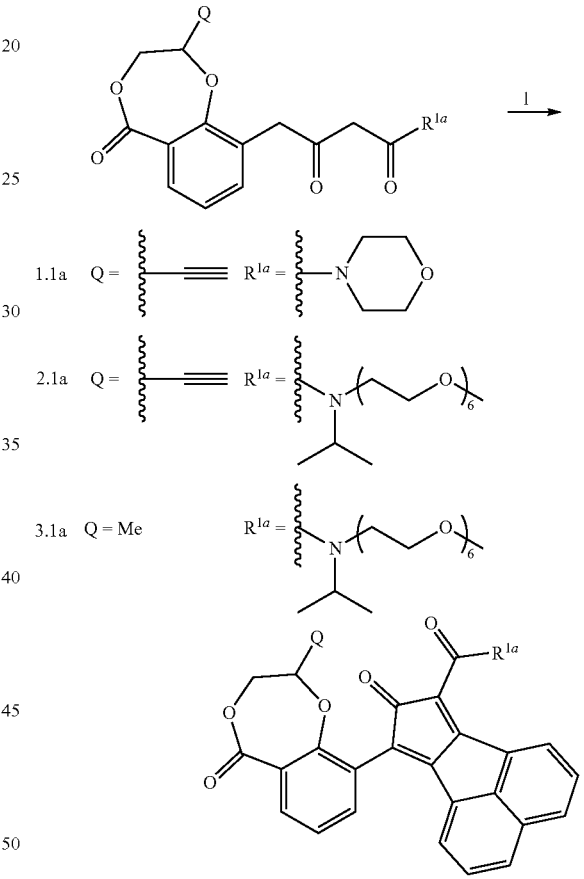

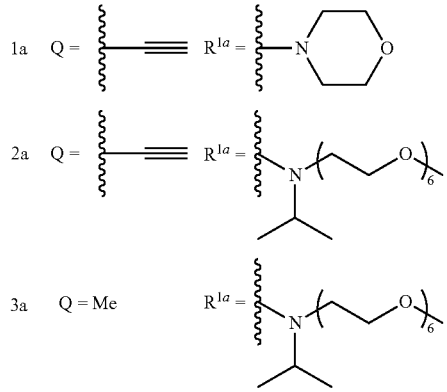

A solution of compound 1.1a, compound 2.1a or compound 3.1a (1 equiv.), acenaphthylene-1, 2-dione (1 equiv.), and Et$_3$N (1.5 equiv.) in THF/MeOH (1:1) was stirred at room temperature overnight. The reaction mixture was then dried under vacuum, and the obtained residue was dissolved in Ac$_2$O (2 mL). The obtained solution was cooled to 0° C., then 1-2 drops of concentrated sulfuric acid was added. The resulting dark purple solution was diluted with ethyl acetate, washed with NaHCO$_3$ solution and brine successively. The obtained organic layer was dried over anhydrous Na$_2$SO$_4$. After filtration and concentration, the residue was purified on a silica gel column to afford compound 1a, 2a or 3a.

Compound 1a (Dark solid. Yield: 64%). $^1$H NMR (CDCl$_3$): δ 8.08 (d, J=7.0 Hz, 1H), 7.99 (d, J=8.2 Hz, 1H), 7.92 (d, J=8.7 Hz, 1H), 7.85 (d, J=7.1 Hz, 1H), 7.81-7.67 (m, 2H), 7.61 (m, 2H), 7.45 (t, J=7.7 Hz, 1H), 5.13 (s, 1H), 4.39 (s, 1H), 4.25 (s, 1H), 3.94-3.70 (m, 6H), 3.58 (d, J=3.0 Hz, 2H), 2.46 (d, J=1.9 Hz, 1H). $^{13}$C NMR (CDCl$_3$): δ 198.8, 171.2, 168.8, 163.5, 162.6, 155.2, 145.6, 136.2, 131.6, 129.7, 129.6, 128.8, 128.0, 125.4, 124.8, 67.2, 66.9, 65.8, 60.4, 47.9, 42.7, 21.7, 15.3, 14.2. HRMS (ESI) [M+H]$^+$ calcd. for C$_{31}$H$_{22}$NO$_6$ 504.1442, found 504.1429.

Compound 2a (Dark sticky oil. Yield: 60%). $^1$H NMR (CD$_3$CN): δ 8.05 (d, J=8.2 Hz, 1H), 8.00 (d, J=8.2 Hz, 1H), 7.90-7.56 (m, 6H), 7.49 (t, J=7.7 Hz, 1H), 5.19 (br, 1H), 4.55-4.41 (m, 1H), 4.26-4.17 (m, 1H), 3.82-3.37 (m, 22H), 3.31 (d, J=5.7 Hz, 5H), 2.95 (s, 0.3H), 2.71 (s, 0.6H), 1.40 (d, J=6.7 Hz, 2H), 1.30 (d, J=7.0 Hz, 0.4H), 1.23-1.17 (m, 3.6H). $^{13}$C NMR (CD$_3$CN): δ 198.9, 168.7, 163.9, 157.7, 150.0, 144.8, 136.0, 131.8, 130.9, 129.6, 128.9, 128.8, 128.0, 125.2, 123.1, 71.6, 70.2, 70.0, 69.8, 68.6, 66.7, 57.9, 50.6, 40.2, 20.9, 20.8, 19.8. HRMS (ESI) [M+H]$^+$ calcd. for C$_{43}$H$_{48}$NO$_{11}$ 754.3222, found 754.3210.

Compound 3a (Dark sticky oil. Yield: 68%). $^1$H NMR (CDCl$_3$): δ 8.00-7.81 (m, 4H), 7.77 (dd, J=17.7, 7.0 Hz, 1H), 7.67 (t, J=7.6 Hz, 1H), 7.63-7.49 (m, 2H), 7.32 (t, J=7.6 Hz, 1H), 4.78-4.55 (m, 2H), 4.23-4.01 (m, 2H), 3.82 (t, J=6.2 Hz, 2H), 3.79-3.50 (m, 20H), 3.50-3.31 (m, 5H), 1.45-1.06 (m, 9H). $^{13}$C NMR (CDCl$_3$): δ 198.8, 169.56 164.3, 159.9, 155.2, 145.3, 136.1, 132.8, 131.7, 130.9, 129.7, 128.9, 128.7, 127.9, 123.6, 117.3, 78.1, 71.9, 70.6, 70.5, 68.9, 59.0, 50.8, 40.6, 21.7, 21.6, 20.6. HRMS (ESI) [M+Na]$^+$ calcd. for C$_{42}$H$_{49}$NO$_{11}$Na 766.3203, found 766.3241.

Example 13

Carbon Monoxide Release from Compounds 1a and 2a

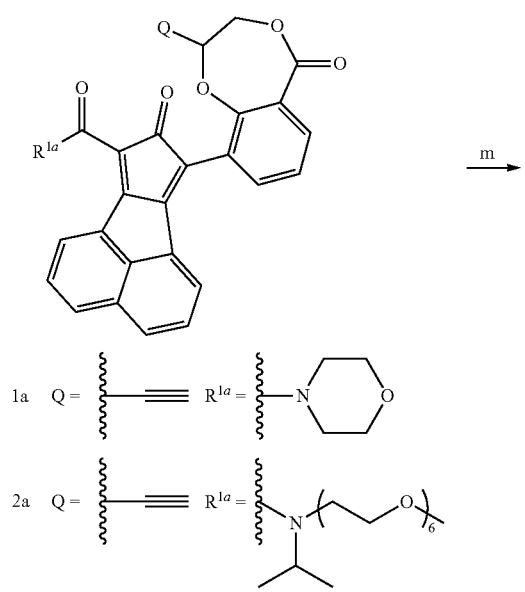

A solution of compound 1a or compound 2a (10 mg) and porcine liver esterase (15 mg) in 30% DMSO/PBS (50 mL) was incubated at 37° C. for 48 h. Then MeOH (60 mL) was added, and the solution was centrifuged to get rid of the protein. The obtained solution was dried under vacuum, and the residue was acidified and extracted with ethyl acetate. The obtained organic layer was dried over anhydrous Na$_2$SO$_4$. After filtration and concentration, the residue was purified on a silica gel column to afford the cyclized compound 1b or cyclized compound 2b.

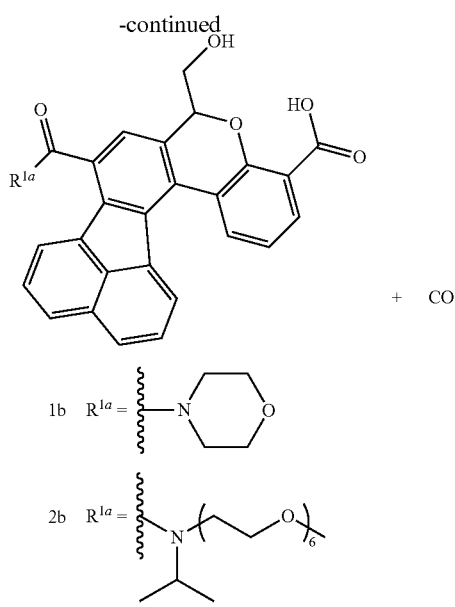

Compound 1b. $^1$H NMR (DMSO-d$_6$): δ 8.46 (d, J=7.6 Hz, 1H), 8.37 (d, J=7.1 Hz, 1H), 8.06 (d, J=8.0 Hz, 2H), 7.91 (d, J=7.0 Hz, 1H), 7.73 (m, 3H), 7.36 (s, 1H), 7.30 (t, J=7.7 Hz, 1H), 5.37 (s, 1H), 3.95-3.75 (m, 4H), 3.60 (m, 4H), 3.39 (s, 1H), 3.19 (d, J=12.3 Hz, 1H). $^{13}$C NMR (DMSO-d$_6$): δ 167.9, 136.6, 133.9, 132.3, 131.7, 130.3, 128.9, 128.6, 128.5, 128.4, 127.6, 123.9, 123.8, 122.9, 121.9, 79.5, 66.4, 61.7, 47.5, 42.0. HRMS (ESI) [M+H]$^+$ calcd. for C$_{30}$H$_{24}$NO$_6$ 494.1598, found 494.1583.

Compound 2b. $^1$H NMR (CD$_3$OD): δ 8.45 (d, J=7.2 Hz, 1H), 8.38 (t, J=8.4 Hz, 1H), 7.99-7.93 (m, 3H), 7.69-7.58 (m, 3H), 7.33-7.22 (m, 2H), 5.39 (br, 1H), 4.11-3.90 (m, 2H), 3.88-3.54 (m, 17H), 3.50-3.38 (m, 4H), 3.28-3.23 (m, 8H), 1.56-1.52 (m, 1.6H), 1.33 (d, J=6.9 Hz, 0.4H), 1.24 (d, J=6.5 Hz, 1H), 1.20 (d, J=6.5 Hz, 1H), 1.14 (d, J=6.5 Hz, 1H), 0.98 (d, J=6.4 Hz, 1H). $^{13}$C NMR (CD$_3$OD): δ 171.2, 150.2, 136.4, 136.1, 135.9, 135.2, 135.2, 134.8, 133.8, 132.5, 131.3, 131.1, 130.9, 130.3, 128.2, 127.9, 127.8, 127.7, 127.4, 123.7, 123.5, 122.4, 122.2, 121.7, 121.4, 79.6, 76.8, 71.4, 70.2, 70.1, 70.0, 69.9, 69.9, 69.8, 69.7, 69.6, 68.7, 68.6, 65.5, 61.3, 57.7, 57.7, 54.8, 51.2, 51.2, 40.5, 33.9, 20.4, 20.3, 20.0, 19.9, 19.4, 19.2, 18.8. HRMS (ESI) [M+H]$^+$ calcd. for C$_{42}$H$_{50}$NO$_{11}$ 744.3378, found 744.3367.

Example 14

Enzyme Triggered Carbon Monoxide Release

The following example describes carbon monoxide release studies for the compounds 1a and 2b.

Figure 2A:
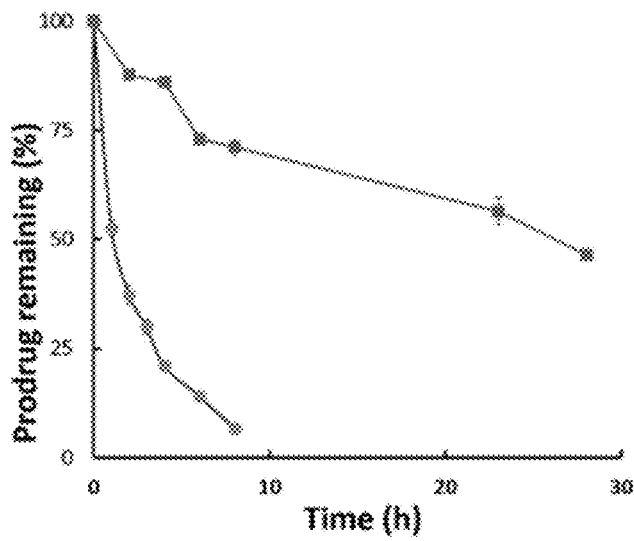
FIG. 2A shows CO release kinetics for 1a (20 µM) with porcine liver esterase (circle) or without porcine liver esterase (square) (10 Unit/mL) in 5% of DMSO/PBS (pH=7.4) at 37° C.
Figure 2B:
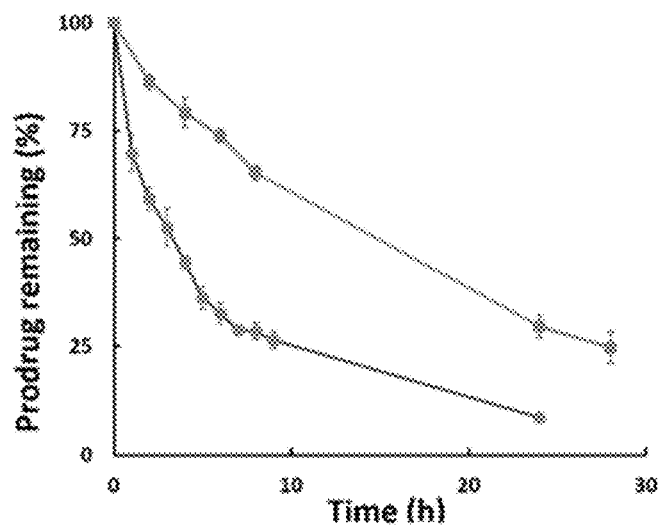
FIG. 2B shows CO release kinetics for 2a (20 µM) with porcine liver esterase (circle) or without porcine liver esterase (square) (10 Unit/mL) in 5% of DMSO/PBS (pH=7.4) at 37° C.

Compounds 1a and 2b readily underwent hydrolysis of the lactone group and cycloaddition to release CO in the presence of porcine liver esterase with half-lives being 1 h and 4 h, respectively (FIGS. 2A and 2B). An illustration of the esterase triggered carbon monoxide release is depicted below in Scheme 3.

Scheme 3

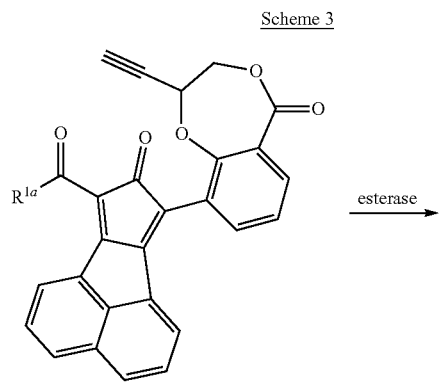

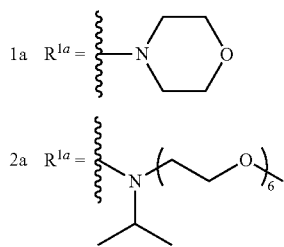

esterase →

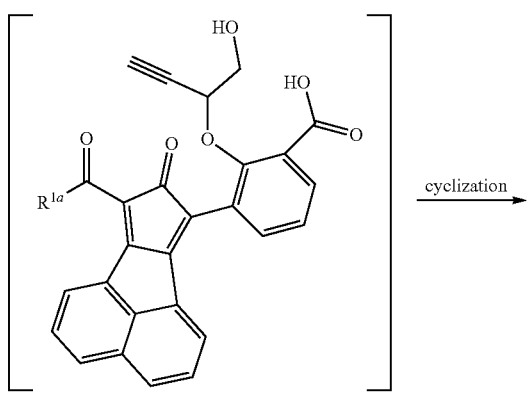

cyclization →

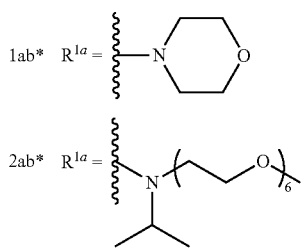

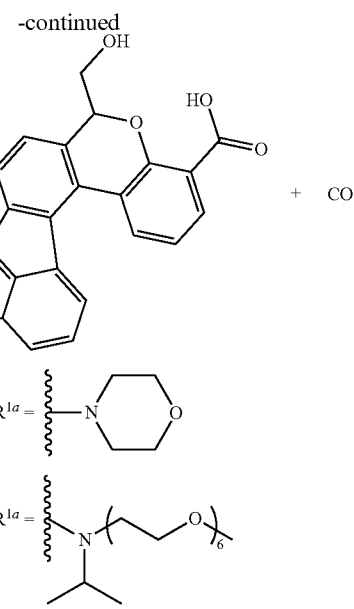

+ CO

The CO release was confirmed both by the thorough characterization of the cyclized product 1b and 2b. Moreover, HPLC studies showed that the hydrolysis intermediate (1ab* and 2ab*, Scheme 3) was not observed throughout the experiment and the cyclized products 1b and 2b were the sole product in the respective reaction, suggesting that the cyclization happened quickly under the experimental conditions, and the enzyme catalyzed hydrolysis is the rate limiting step. Meanwhile, in the absence of an esterase, the lactone hydrolysis of 1a and 2a is quite sluggish with a half-life of around 24 h or 17 h, respectively (FIG. 2B-C, square symbols). This also indicates that the 7-membered lactone ring of 1a and 2a holds the conformation of the alkyne in a position which disfavors the cycloaddition, confirming that cyclized products 1b and 2b cannot form without hydrolysis using an enzyme.

Figure 3:
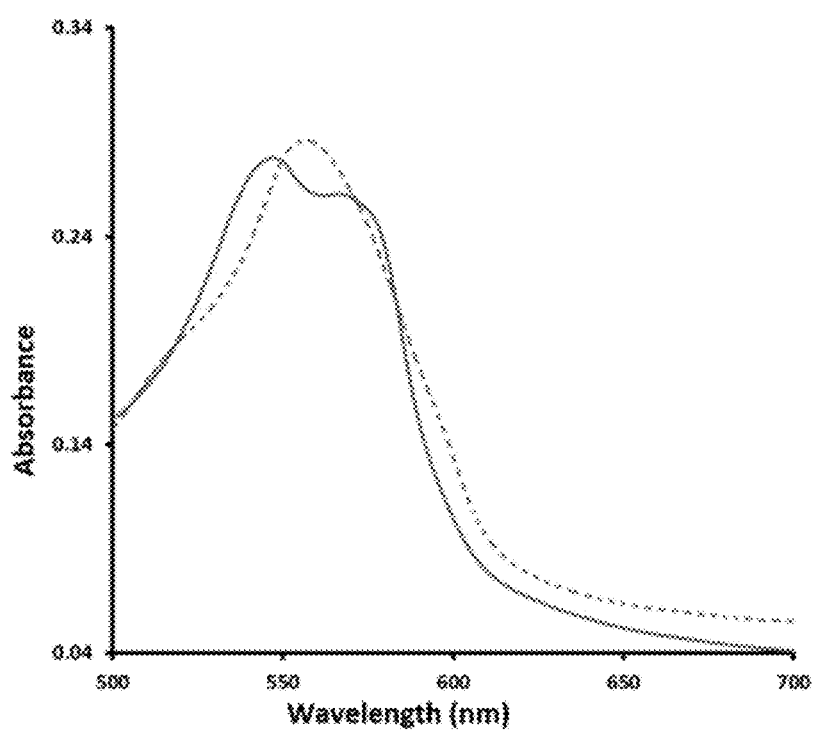
FIG. 3. UV-vis spectra of the CO-myoglobin assay results for 1a. The dashed line represents the absorbance spectrum of the deoxymyoglobin control. The solid line represents the absorbance spectrum of a solution of deoxymyoglobin and compound 1a having been exposed to esterase.

In order to further confirm carbon monoxide release, 1a was chosen for CO-myoglobin assay (FIG. 3). For such purpose, a solution of myoglobin (0.5 mg/ml) and esterase (10 Unit/mL) in PBS (10 mL, pH=7.4) was degassed by bubbling with nitrogen for at least 20 min. To this degassed solution was added a solution of 1a (0.45 mg) in DMSO (1 mL), and the resulting solution was incubated at 37° C. for 4 h. Then a solution of sodium dithionite (1 mL, 22 mg/mL) was added, and a red solution was obtained, which was cooled down to 0° C. with an ice bath, and was stirred for another 1 h. Afterwards, the UV-vis spectra of the resulting pinkish red solution was taken to confirm CO release. The results are shown in FIG. 3.

Example 15

Cytotoxicity Results of Compounds 1a and 2a

The following example describes cytotoxicity assays for the compounds 1a and 2a.

Figure 4A:
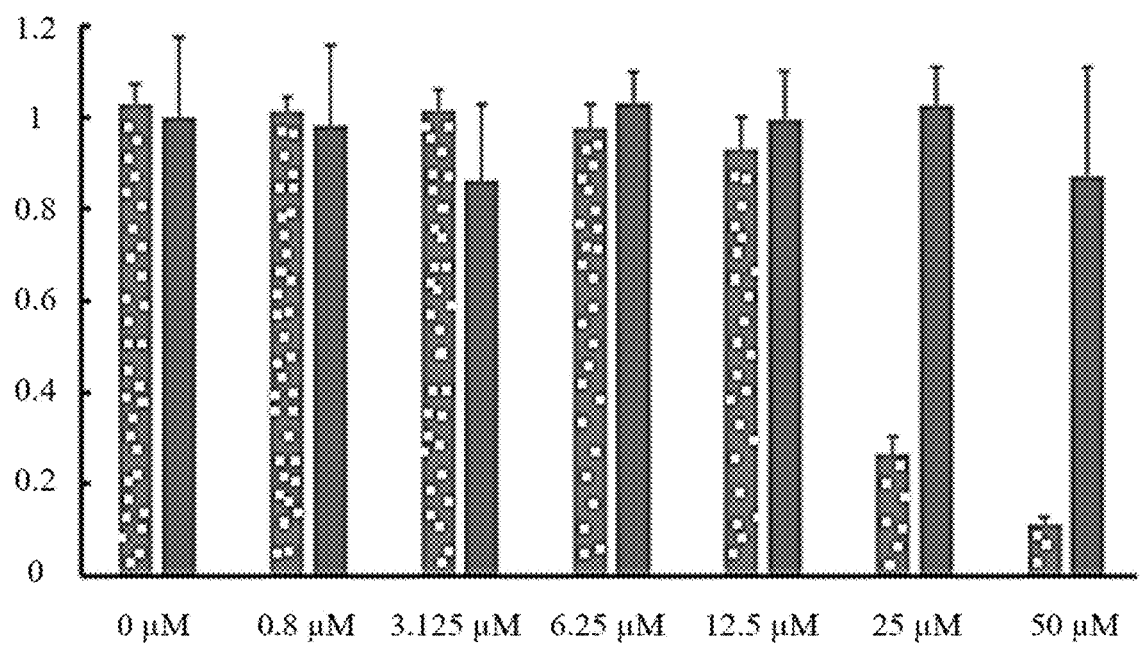
FIG. 4A shows MTT assay results for compounds 1a/1b. Spotted bars=1a; solid bars=1b.
Figure 4B:
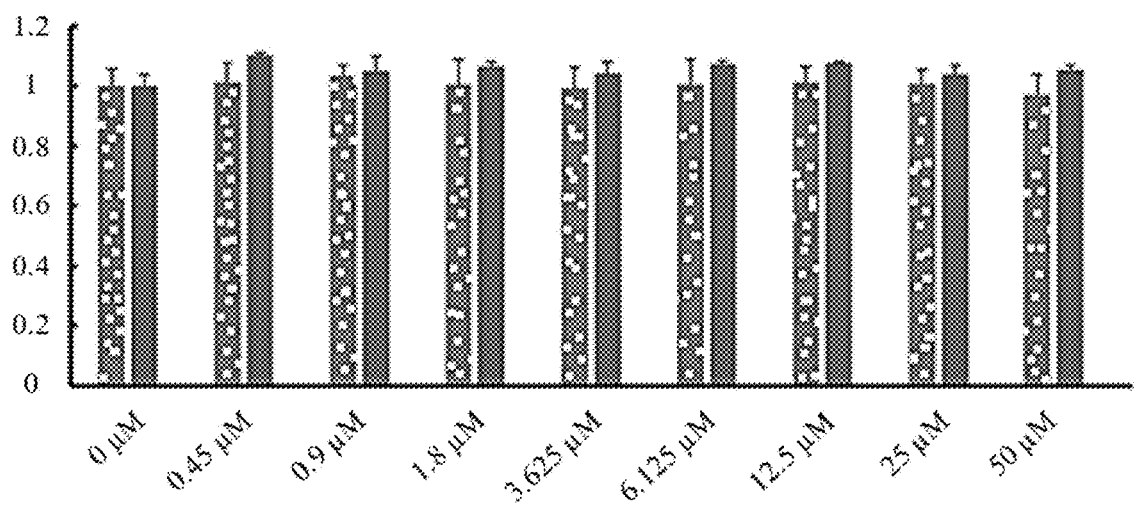
FIG. 4B shows MTT assay results for compounds 2a. Spotted bars=2a; solid bars=1b, 2b.

Raw 264.7 cells were seeded in 96-well plates and cultured in Dulbecco's modified Eagle's medium (DMEM) supplemented with 10% fetal bovine serum (FBS) and 1% penicillin/streptomycin at 37° C. under 5% $CO_2$ for 24 h. Then RAW 264.7 cells were incubated in DMEM containing 1% DMSO and compounds 1a and 2a (0-50 μM) for 24 hours. Then 10 μL of MTT solution was added to each well and incubated for another three hours at 37° C. The absorbance at 570 nm was measured by using a microplate reader. The cell viability was measured. The cytotoxicity results for 1a/1b (spotted bars=1a; solid bars=1b) are shown in FIG. 4A, and the cytotoxicity results for 2a/2b (spotted bars=2a; solid bars=2b) are shown in FIG. 4B.

Example 16

Anti-Inflammation Effects of Compounds 1a and 2a

Having confirmed that 1a and 2a could release carbon monoxide in response to an esterase, the anti-inflammatory effects of the compounds were explored. Specifically, the response of the compounds to intracellular esterase were studied in order to quantify the amount of carbon monoxide released from the compounds. RAW 264.7 cells were seeded in 48-well plates one day before the experiment. Lipopolysaccharides (LPS) were used to initiate the inflammatory response in RAW 264.7 cells. To this end, Raw 264.7 cells were pretreated with different concentrations of 1a, 1b, 2a, 2b or 3a for 4 h, and then were challenged with LPS (1 µg/mL) for 1 h. The cell culture supernatant was collected 1 hour after LPS treatment. Cell culture without LPS treatment was used as the control. The tumor necrosis factor alpha (TNF-α) levels in the cell culture supernatant were measurement by a commercial ELISA kit (ELISA Ready-SET-Go!®-eBioscience).

Figure 5:
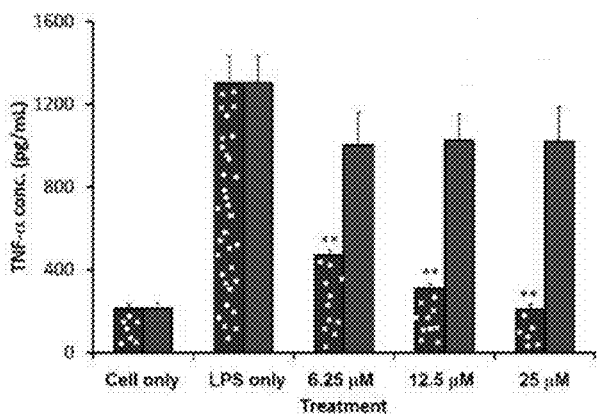
FIG. 5 shows TNF-α suppression effects of 1a, 1b, 2a, 2b and 3a in LPS challenged Raw264.7 cells. Top panel: anti-inflammation results for 1a/1b. Middle panel: anti-inflammation results for 2a/2b. Bottom panel: anti-inflammation results for 3a. Spotted bars=1a, 2a, 3a; solid bars=1b, 2b.
Figure 5:
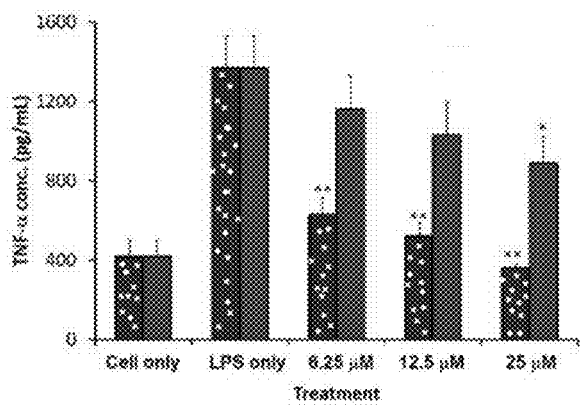
Figure 5:
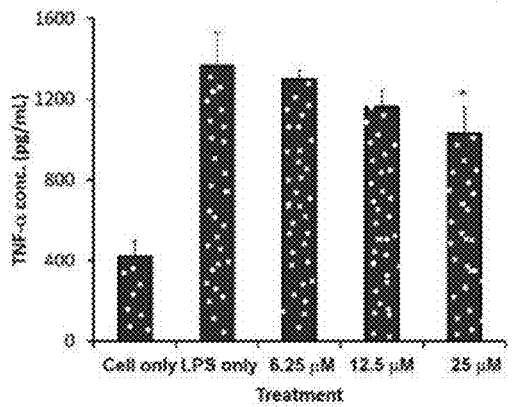

As shown in FIGS. 5A and 5B, both 1a and 2a dose-dependently inhibited the LPS-induced TNF-α secretion. Furthermore, there was no change in cell viability observed in the ELISA experiment for both 1a and 2a. Meanwhile, their cyclized products after CO release showed no similar effects, except for 2b, which showed some TNF-α inhibition effect at 25 µM (FIG. 5B). As an additional control, the cells were also pretreated with 3a, which is analogous to the prodrugs 1a and 2a, without the alkyne moiety. As expected, 3a did not present meaningful anti-inflammatory effect until the concentration reached 25 µM (FIG. 5C). Such results indicate that the observed effects were resulted from the released CO, and that prodrug 1a and 2a released a sufficient amount of CO to suppress TNF-α production.

Example 17

Fluorescent Imaging of CO Release

Figure 6A:
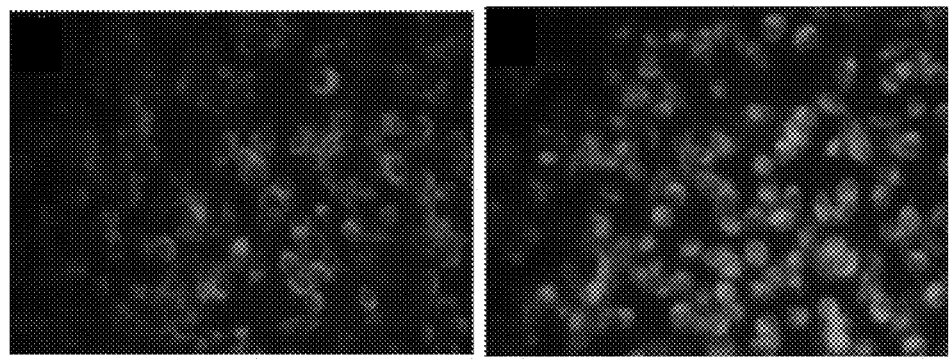
FIG. 6A shows the visualization of intracellular CO release from 2a using COP-1. Left panel: COP-1 (1 µM)+2a (25 µM). Right panel: COP-1 (1 µM)+2a (50 µM).
Figure 6B:
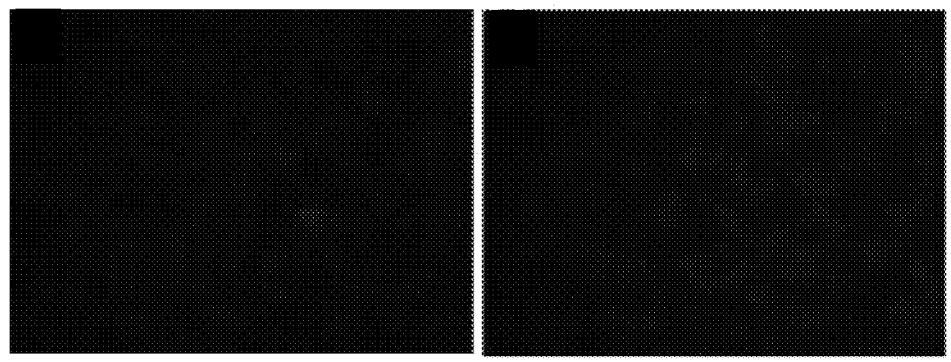
FIG. 6B shows the visualization of intracellular CO release under control conditions. Left panel: COP-1 (1 µM) only. Right panel: COP-1 (1 µM)+3a (50 µM).
Figure 6C:
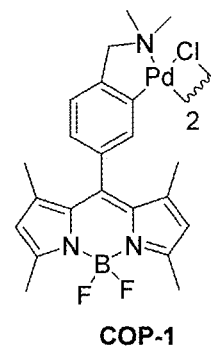
FIG. 6C shows the structure of COP-1.
Figure 7:
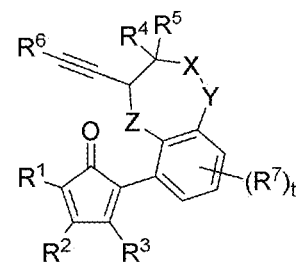
FIG. 7 shows the structure of carbon monoxide-releasing compounds.

To confirm intracellular CO release, a reported CO fluorescent probe COP-1 was employed to visualize CO release from 2a. COP-1 is described, for example, by Michel, et al. (J. Am. Chem. Soc. 2012, 134, 15668-15671). RAW 264.7 cells were seeded in the 6-well plate one day before the imaging experiment. Compounds were dissolved in DMSO as stock solution. Final concentration of 1 µM COP-1 and different concentrations of 2a and 3a (25 µM, 50 µM) were added into the cell culture. After adding the compound, the cells were incubated under 37° C. for 5 hours. The cell samples were then fixed for imaging study under FITC channel (excitation: 490 nm, emission: 525 nm) for the fluorescence of COP-1, using a Zeiss fluorescent microscope. As shown in FIG. 6, the cells cotreated with COP-1 and 2a dose-dependently showed increase in fluorescence intensity (FIG. 6A), and the cells treated with probe only or 3a showed no fluorescence (FIG. 6B), indicating intracellular CO release from 2a.

IX. Exemplary Embodiments

Exemplary embodiments provided in accordance with the presently disclosed subject matter include, but are not limited to, the claims and the following embodiments:

1. A compound comprising a cyclopentadienone moiety, a non-reactive dienophile, and an enzyme-cleavable tethering moiety connecting the cyclopentadienone moiety to the non-reactive dienophile, wherein cleavage of the enzyme-cleavable tethering moiety results in conversion of the non-reactive dienophile to a reactive dienophile.

2. A compound according to Formula I:

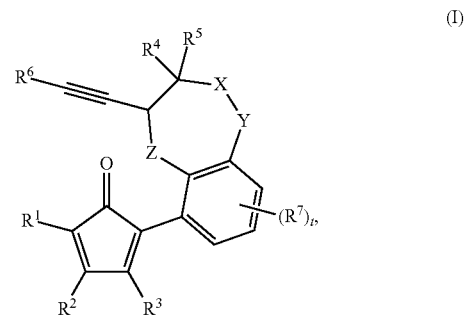

or a pharmaceutically acceptable salt thereof, wherein:

the moiety —X—Y— is selected from the group consisting of —C(O)—O— and —O—C(O)—;

Z is selected from the group consisting of —O— and —S—;

$R^1$ is selected from the group consisting of H, $C_{1-8}$ alkyl, $C_{3-8}$ cycloalkyl, $C_{6-10}$ aryl, and —C(O)$R^{1a}$;

$R^{1a}$ is selected from the group consisting of $C_{1-8}$ alkyl, $C_{3-8}$ cycloalkyl, $C_{6-10}$ aryl, 3- to 8-membered heterocyclyl, 5- to 12-membered heteroaryl, $NR^{1b}R^{1c}$, —$OR^{1b}$, and a solubilizing moiety;

$R^{1b}$ and $R^{1c}$ are independently selected from H, $C_{1-8}$ alkyl, $C_{3-8}$ cycloalkyl, and a solubilizing moiety;

$R^2$ and $R^3$ are independently selected $C_{6-10}$ aryl, or $R^2$ and $R^3$ are optionally taken together to form a fused tricyclic moiety;

$R^4$, $R^5$, and $R^6$ are independently selected from the group consisting of H and $C_{1-6}$ alkyl;

$R^1$, $R^2$, $R^3$, $R^4$, $R^5$, and $R^6$ are optionally and independently substituted with one or more $R^7$;

each $R^7$ is independently selected from the group consisting of $C_{1-4}$ alkyl, halogen, —CN, —$OR^a$, —C(O)$R^b$, —C(O)$OR^a$, —OC(O)$R^b$, —N($R^a$)$_2$, $NR^aC(O)R^b$, —C(O)N($R^a$)$_2$, —S(O)$R^b$, —S(O)$_2R^b$, —S(O)$_2OR^a$, —S(O)$_2N(R^a)_2$, and —$NR^aS(O)_2R^b$;

each $R^a$ is independently selected from the group consisting of H and $C_{1-4}$ alkyl;

each $R^b$ is $C_{1-4}$ alkyl; and subscript t is 0, 1, 2, or 3.

3. The compound of embodiment 2, or a pharmaceutically acceptable salt thereof, wherein the moiety —X—Y— is —O—C(O)—.

4. The compound of embodiment 2 or embodiment 3, or a pharmaceutically acceptable salt thereof, wherein $R^2$ and $R^3$ are taken together to form a fused tricyclic moiety.

5. The compound of embodiment 2, or a pharmaceutically acceptable salt thereof, having a structure according to Formula Ia:

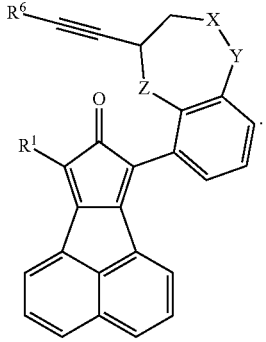

(Ia)

6. The compound of embodiment 5, or a pharmaceutically acceptable salt thereof, having a structure according to Formula Ib:

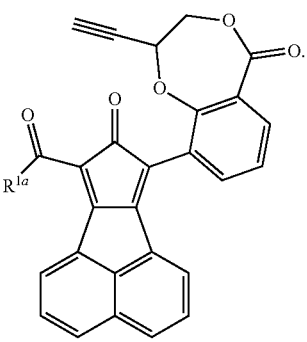

(Ib)

7. The compound of any one of embodiments 2-6, or a pharmaceutically acceptable salt thereof, wherein $R^{1a}$ is selected from the group consisting of 3- to 8-membered heterocyclyl and —$NR^{1b}R^{1c}$;
$R^{1b}$ is selected from H and $C_{1-8}$ alkyl; and
$R^{1c}$ is selected from H, $C_{1-8}$ alkyl, and a solubilizing moiety.
8. The compound of embodiment 7, or a pharmaceutically acceptable salt thereof, wherein the solubilizing moiety is selected from the group consisting of an oligo(ethylene glycol), a poly(ethylene glycol), and a monosaccharide.
9. The compound of embodiment 2, which is selected from the group consisting of:

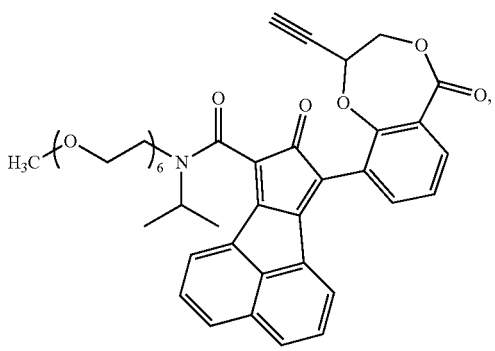

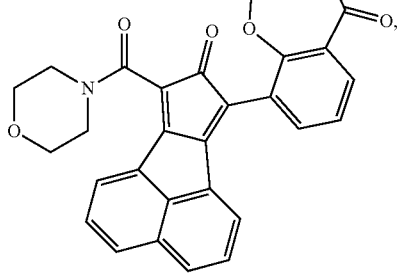

and pharmaceutically acceptable salts thereof.

10. A pharmaceutical composition comprising a compound according to any one of embodiments 1-9 and a pharmaceutically acceptable excipient.
11. A method for delivering carbon monoxide to a subject in need thereof, the method comprising administering to the subject a compound according to any one of embodiments 1-9 or a pharmaceutical composition according to embodiment 10.
12. A method for treating a disease or condition, the method comprising administering to a subject in need thereof an effective amount of a compound according to any one of embodiments 1-9 or an effective amount of a pharmaceutical composition according to embodiment 10.
13. The method of embodiment 12, wherein the disease or condition is selected from the group consisting of inflammation, cancer, organ transplantation, bacterial infection, and thrombosis.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:
1. A compound having a structure according to Formula I:

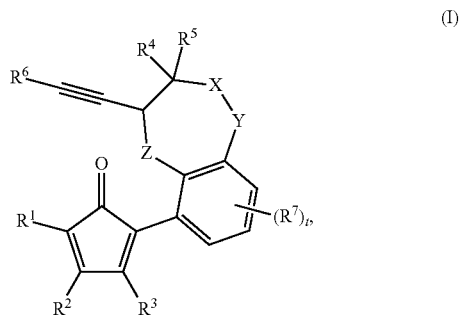

(I)

or a pharmaceutically acceptable salt thereof, wherein:
the moiety —X—Y— is selected from the group consisting of —O—C(O)— and —C(O)—O—;
Z is selected from the group consisting of —O— and —S—;
$R^1$ is selected from the group consisting of —C(O)$R^{1a}$, H, $C_{1-8}$ alkyl, $C_{3-8}$ cycloalkyl, and $C_{6-10}$ aryl;

$R^{1a}$ is selected from the group consisting of —$NR^{1b}R^{1c}$, $C_{1-8}$ alkyl, $C_{3-8}$ cycloalkyl, $C_{6-10}$ aryl, 3- to 8-membered heterocyclyl, 5- to 12-membered heteroaryl, —$OR^{1b}$, and a solubilizing moiety;

$R^{1b}$ and $R^{1c}$ are independently selected from H, $C_{1-8}$ alkyl, $C_{3-8}$ cycloalkyl, and a solubilizing moiety;

$R^2$ and $R^3$ are taken together to form a fused tricyclic moiety, or $R^2$ and $R^3$ are independently $C_{6-10}$ aryl;

$R^4$, $R^5$, and $R^6$ are independently selected from the group consisting of H and $C_{1-6}$ alkyl;

$R^1$, $R^2$, $R^3$, $R^4$, $R^5$, and $R^6$ are optionally and independently substituted with one or more $R^7$;

each $R^7$ is independently selected from the group consisting of $C_{1-4}$ alkyl, halogen, —CN, —$OR^a$, —$C(O)R^b$, —$C(O)OR^a$, —$OC(O)R^b$, —$N(R^a)_2$, —$NR^aC(O)R^b$, —$C(O)N(R^a)_2$, —$S(O)R^b$, —$S(O)_2R^b$, —$S(O)_2OR^a$, —$S(O)_2N(R^a)_2$, and —$NR^aS(O)_2R^b$;

each $R^a$ is independently selected from the group consisting of H and $C_{1-4}$ alkyl;

each $R^b$ is $C_{1-4}$ alkyl; and subscript t is 0, 1, 2, or 3.

2. The compound of claim 1, or a pharmaceutically acceptable salt thereof, wherein the moiety —X—Y— is —O—C(O)—.

3. The compound of claim 1, or a pharmaceutically acceptable salt thereof, wherein $R^2$ and $R^3$ are taken together to form a fused tricyclic moiety.

4. The compound of claim 1, or a pharmaceutically acceptable salt thereof, having a structure according to Formula Ia:

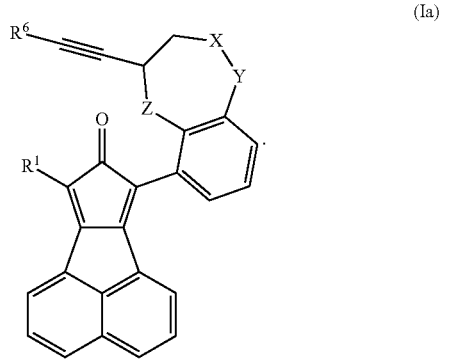

(Ia)

5. The compound of claim 4, or a pharmaceutically acceptable salt thereof, having a structure according to Formula Ib:

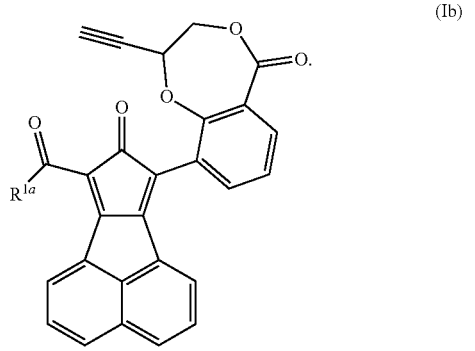

(Ib)

6. The compound of claim 1, or a pharmaceutically acceptable salt thereof, wherein $R^{1a}$ is selected from the group consisting of 3- to 8-membered heterocyclyl and —$NR^{1b}R^{1c}$;

$R^{1b}$ is selected from H and $C_{1-8}$ alkyl; and $R^{1c}$ is selected from H, $C_{1-8}$ alkyl, and a solubilizing moiety.

7. The compound of claim 6, or a pharmaceutically acceptable salt thereof, wherein the solubilizing moiety is selected from the group consisting of an oligo(ethylene glycol), a poly(ethylene glycol), and a monosaccharide.

8. The compound of claim 1, which is selected from the group consisting of:

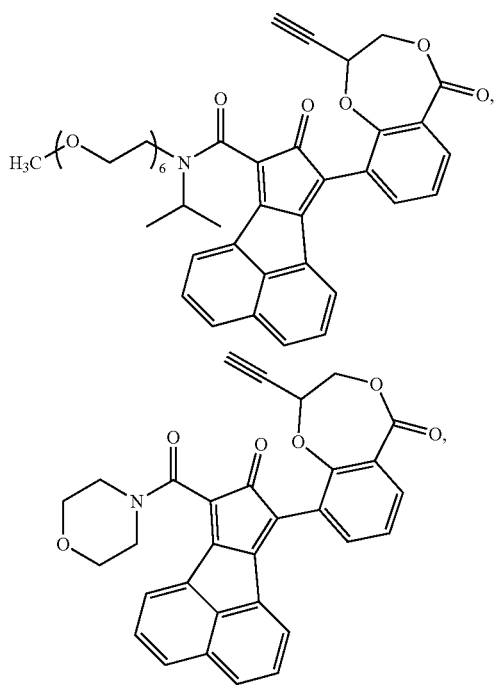

and pharmaceutically acceptable salts thereof.

9. A pharmaceutical composition comprising a compound according to claim 1 and a pharmaceutically acceptable excipient.

10. A method for delivering carbon monoxide to a subject in need thereof, the method comprising administering to the subject a compound having a structure according to Formula I:

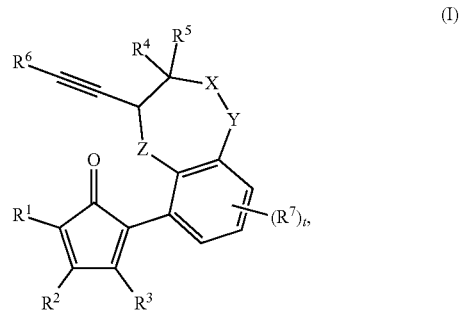

(I)

or a pharmaceutically acceptable salt thereof, wherein:
the moiety —X—Y— is selected from the group consisting of —O—C(O)— and —C(O)—O—;

Z is selected from the group consisting of —O— and —S—;

$R^1$ is selected from the group consisting of —C(O)$R^{1a}$, H, $C_{1-8}$ alkyl, $C_{3-8}$ cycloalkyl, and $C_{6-10}$ aryl;

$R^{1a}$ is selected from the group consisting of —$NR^{1b}R^{1c}$, $C_{1-8}$ alkyl, $C_{3-8}$ cycloalkyl, $C_{6-10}$ aryl, 3- to 8-membered heterocyclyl, 5- to 12-membered heteroaryl, —$OR^{1b}$, and a solubilizing moiety;

$R^{1b}$ and $R^{1c}$ are independently selected from H, $C_{1-8}$ alkyl, $C_{3-8}$ cycloalkyl, and a solubilizing moiety;

$R^2$ and $R^3$ are taken together to form a fused tricyclic moiety, or $R^2$ and $R^3$ are independently $C_{6-10}$ aryl;

$R^4$, $R^5$, and $R^6$ are independently selected from the group consisting of H and $C_{1-6}$ alkyl;

$R^1$, $R^2$, $R^3$, $R^4$, $R^5$, and $R^6$ are optionally and independently substituted with one or more $R^7$;

each $R^7$ is independently selected from the group consisting of $C_{1-4}$ alkyl, halogen, —CN, —$OR^a$, —C(O)$R^b$, —C(O)$OR^a$, —OC(O)$R^b$, —N($R^a$)$_2$, —$NR^a$C(O)$R^b$, —C(O)N($R^a$)$_2$, —S(O)$R^b$, —S(O)$_2R^b$, —S(O)$_2OR^a$, —S(O)$_2$N($R^a$)$_2$, and —$NR^a$S(O)$_2R^b$;

each $R^a$ is independently selected from the group consisting of H and $C_{1-4}$ alkyl;

each $R^b$ is $C_{1-4}$ alkyl; and subscript t is 0, 1, 2, or 3.

11. A method for treating a disease or condition, the method comprising administering to a subject having said disease or condition an effective amount of a compound having a structure according to Formula I:

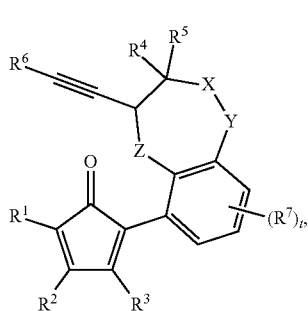

(I)

or a pharmaceutically acceptable salt thereof, wherein the disease or condition is selected from the group consisting of a cardiovascular condition, an ophthalmic condition, a neurological condition, a urological condition, diabetes, inflammation, bacterial infection, hypertension, hypothermia, asthma, gastric injury, irritable bowel syndrome, kidney dysfunction, sepsis, ischemia, respiratory distress syndrome, autoimmune disorders, thrombosis, cancer, wounds, and rejection in organ transplantation;

and wherein:

the moiety —X—Y— is selected from the group consisting of —O—C(O)— and —C(O)—O—;

Z is selected from the group consisting of —O— and —S—;

$R^1$ is selected from the group consisting of —C(O)$R^{1a}$, H, $C_{1-8}$ alkyl, $C_{3-8}$ cycloalkyl, and $C_{6-10}$ and;

$R^{1a}$ is selected from the group consisting of —$NR^{1b}R^{1c}$, $C_{1-8}$ alkyl, $C_{3-8}$ cycloalkyl, $C_{6-10}$ aryl, 3- to 8-membered heterocyclyl, 5- to 12-membered heteroaryl, —$OR^{1b}$, and a solubilizing moiety;

$R^{1b}$ and $R^{1c}$ are independently selected from H, $C_{1-8}$ alkyl, $C_{3-8}$ cycloalkyl, and a solubilizing moiety;

$R^2$ and $R^3$ are taken together to form a fused tricyclic moiety, or $R^2$ and $R^3$ are independently $C_{6-10}$ aryl;

$R^4$, $R^5$, and $R^6$ are independently selected from the group consisting of H and $C_{1-6}$ alkyl;

$R^1$, $R^2$, $R^3$, $R^4$, $R^5$, and $R^6$ are optionally and independently substituted with one or more $R^7$;

each $R^7$ is independently selected from the group consisting of $C_{1-4}$ alkyl, halogen, —CN, —$OR^a$, —C(O)$R^b$, —C(O)$OR^a$, —OC(O)$R^b$, —N($R^a$)$_2$, —$NR^a$C(O)$R^b$, —C(O)N($R^a$)$_2$, —S(O)$R^b$, —S(O)$_2R^b$, —S(O)$_2OR^a$, —S(O)$_2$N($R^a$)$_2$, and —$NR^a$S(O)$_2R^b$;

each $R^a$ is independently selected from the group consisting of H and $C_{1-4}$ alkyl;

each $R^b$ is $C_{1-4}$ alkyl; and subscript t is 0, 1, 2, or 3.

12. The method of claim 11, wherein the disease or condition is selected from the group consisting of inflammation, cancer, rejection in organ transplantation, bacterial infection, and thrombosis.

* * * * *

UNITED STATES PATENT AND TRADEMARK OFFICE
CERTIFICATE OF CORRECTION

| | | |
|---|---|---|
| PATENT NO. | : 11,377,435 B2 | Page 1 of 1 |
| APPLICATION NO. | : 16/712639 | |
| DATED | : July 5, 2022 | |
| INVENTOR(S) | : Binghe Wang et al. | |

It is certified that error appears in the above-identified patent and that said Letters Patent is hereby corrected as shown below:

In the Claims

In Column 54, Line 16, in Claim 11, delete "and;" and insert -- aryl; --.

Signed and Sealed this
Thirteenth Day of February, 2024

*Katherine Kelly Vidal*

Katherine Kelly Vidal
*Director of the United States Patent and Trademark Office*